United States Patent [19]
Morishita et al.

[11] Patent Number: 4,716,153
[45] Date of Patent: Dec. 29, 1987

[54] STABLE ORAL PREPARATION OF MACROLIDE ANTIBIOTICS AND METHOD FOR STABILIZING THE SAME

[75] Inventors: Masataka Morishita; Masaru Ono; Yukio Sumita, all of Shizuoka, Japan

[73] Assignee: Toyo Jozo Company, Ltd., Shizuoka, Japan

[21] Appl. No.: 900,231

[22] Filed: Aug. 25, 1986

Related U.S. Application Data

[63] Continuation of Ser. No. 555,378, Nov. 28, 1983, abandoned.

[30] Foreign Application Priority Data

Dec. 4, 1982 [JP] Japan .................. 57-212942

[51] Int. Cl.$^4$ .................. A61K 31/70; A61K 31/19; A61K 37/44; A61K 35/00
[52] U.S. Cl. .................. 514/30; 514/557; 514/561; 424/115; 424/154; 424/155; 424/156; 424/157
[58] Field of Search .................. 514/23, 30, 561, 557; 424/115, 154–157

[56] References Cited

U.S. PATENT DOCUMENTS

| | | | |
|---|---|---|---|
| 3,891,752 | 6/1975 | Gorton et al. | 424/117 |
| 3,962,419 | 6/1976 | Mayama et al. | 424/78 |
| 4,064,230 | 12/1977 | Gordon et al. | 424/19 |
| 4,102,999 | 7/1978 | Umezowa et al. | 424/123 |
| 4,127,647 | 11/1978 | Sato et al. | 424/78 |
| 4,137,307 | 1/1979 | Funakoshi et al. | 514/2 |
| 4,327,086 | 4/1982 | Fukushima et al. | 514/2 |
| 4,338,335 | 7/1982 | McAleer et al. | 514/777 |

FOREIGN PATENT DOCUMENTS

| | | |
|---|---|---|
| 0010297 | 4/1980 | European Pat. Off. |
| 46-35392 | 10/1971 | Japan |
| 53-01328 | 1/1978 | Japan |
| 54-115389 | 6/1979 | Japan |
| 55-57600 | 4/1980 | Japan |
| 3547610 | 12/1980 | Japan |

OTHER PUBLICATIONS

Merck Index, 9th Ed., No. 2307, 1976.
Chem Pharm Bull. 16, 1402, 1968.
J. Antibiot. 29, 536, 1976.
Chem. Pharm. Bull. 1099, 1962.
Journal of Antibiotics, 28:401 (1975) Chemical & Biol. Studies on 16 Membered Macrolide Antibiotics.
French Search Report.

*Primary Examiner*—J. R. Brown
*Assistant Examiner*—John W. Rollins
*Attorney, Agent, or Firm*—Ladas & Parry

[57] ABSTRACT

Stable oral preparations of 16-membered ring macrolide antibiotics such as SF-837, josamycin, 3"-propionyljosamycin, by incorporating stabilizers showing pH 3–10 in an aqueous medium, such as glycine, and dissolution accelerators showing pH 2.5–4 in an aqueous medium such as citric acid or tartaric acid. Coating such dissolution accelerators with a film-forming substance is useful to enhance the stability of the oral preparation of such antibiotics.

18 Claims, 35 Drawing Figures

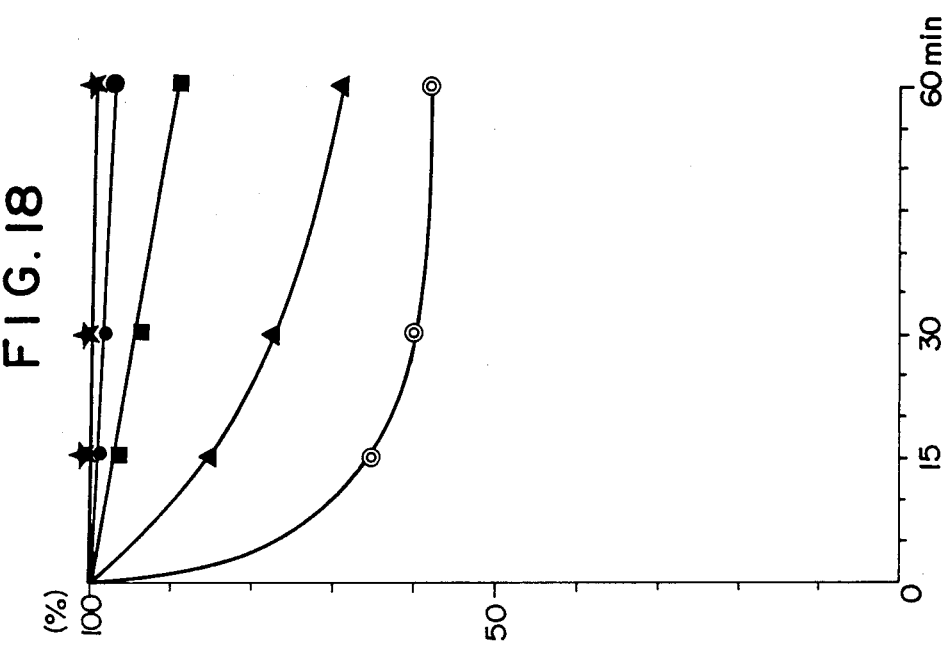
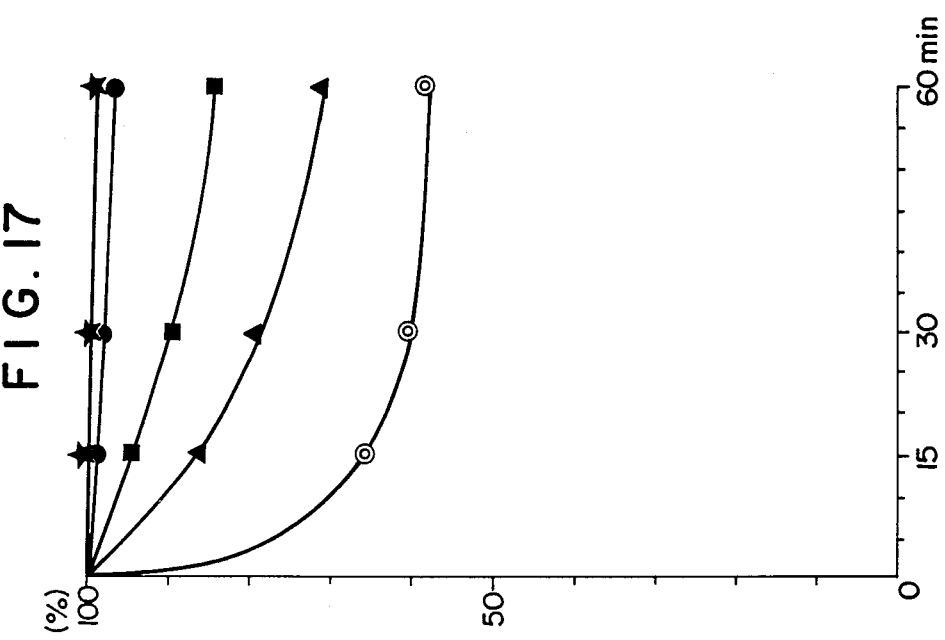

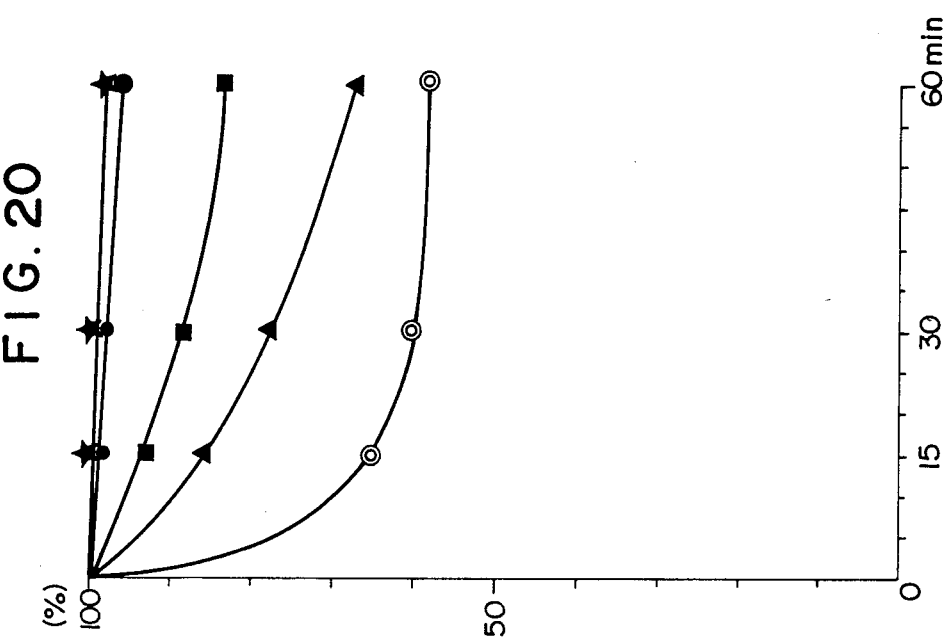
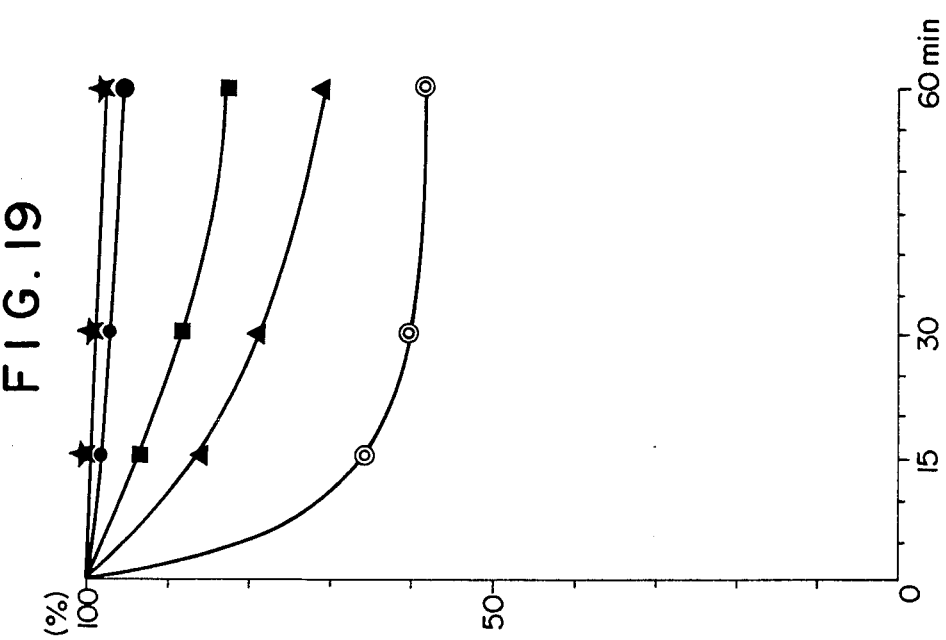

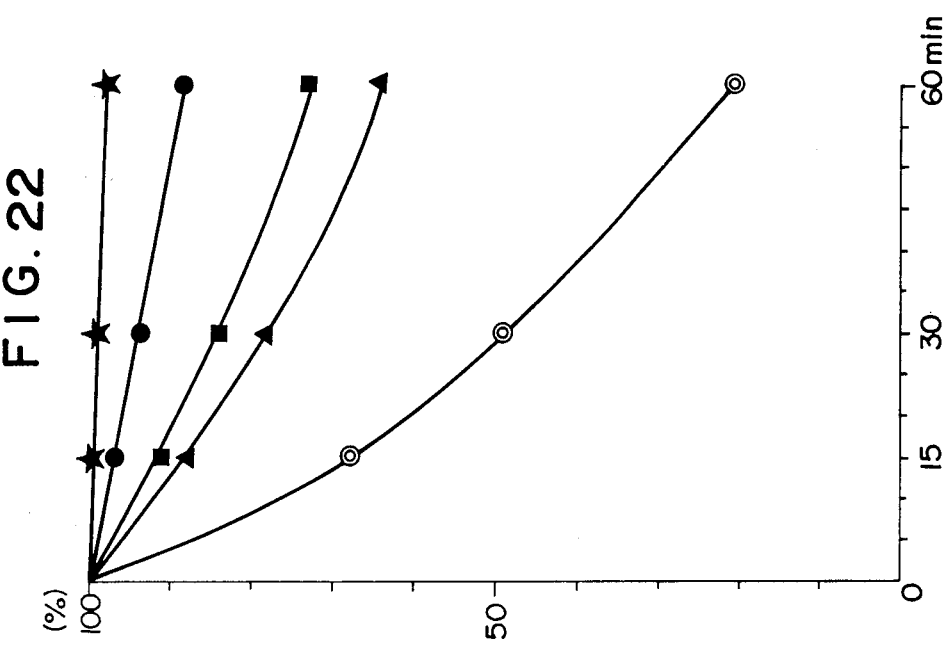
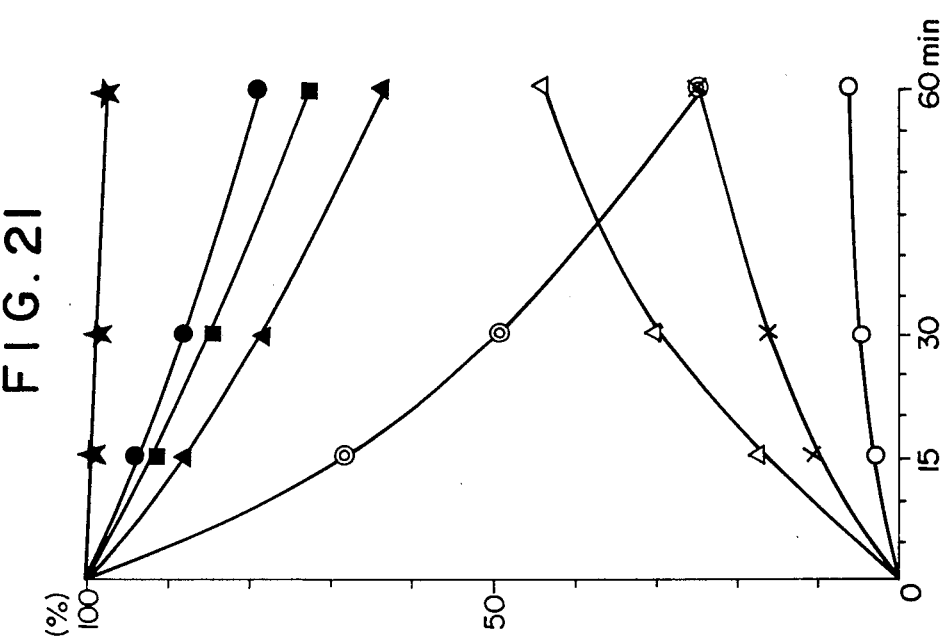

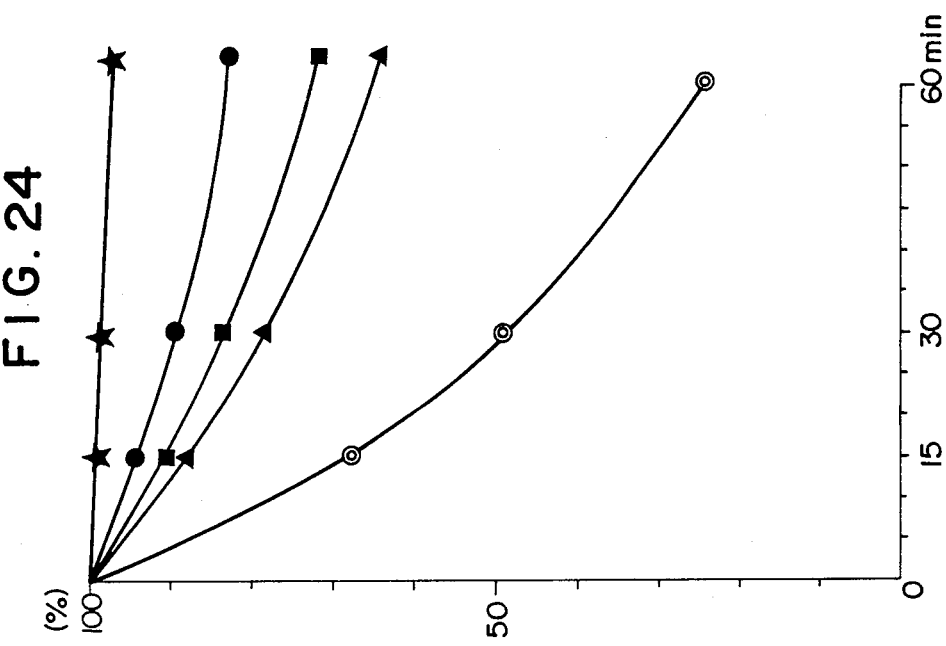
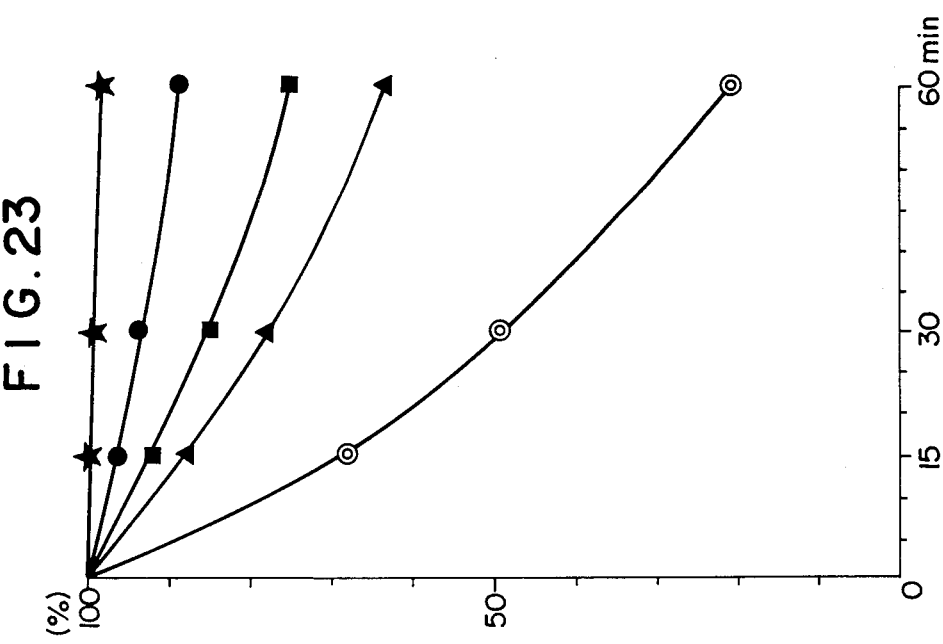

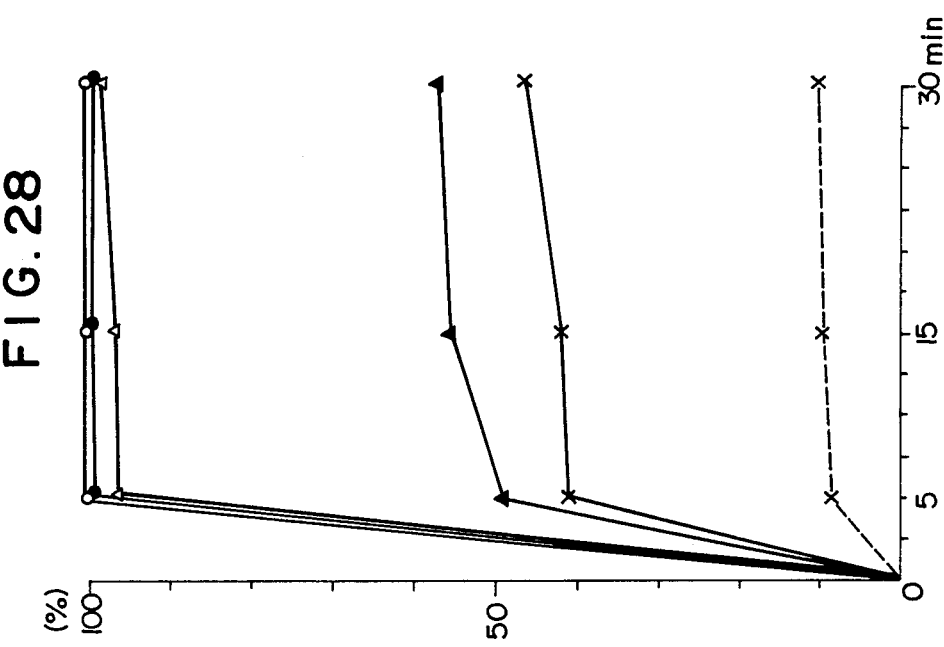
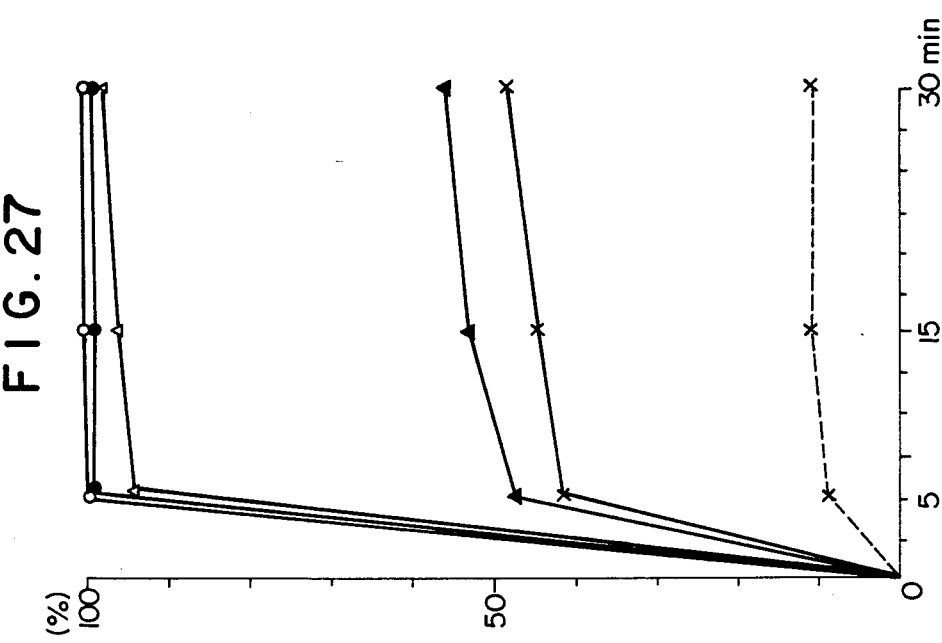

STABLE ORAL PREPARATION OF MACROLIDE ANTIBIOTICS AND METHOD FOR STABILIZING THE SAME

This is a continuation of co-pending application Ser. No. 555,378 filed on Nov. 28, 1983, now abandoned.

The present invention relates to a stable oral preparation of 16-membered ring macrolide antibiotics and a method for stabilizing the same.

Sixteen-membered ring macrolide antibiotics, for example, leucomycin [Chem. Pharm. Bull., 16, 1402 (1968)], SF-837 (Midecamycin, J. Antibiot., 29, 536 (1976)]and 9,3"-diacetyl-SF-837 (Japanese Patent Application No. 54-115389) have been reported to undergo an allyl rearrangement reaction and a demycarose reaction after an acidic treatment. Thus 16-membered ring macrolide antibiotics are generally unstable in an acidic region. For example, SF-837 (hereinafter referred to as 'midecamycin') is unstable when dissolved in Japanese Pharmacopoeia 1st solution (pH 1.2) (hereinafter referred to "1st solution"), showing the progress of decomposition in a short time to produce 9-deoxy-10,12-dedieno-9,11-diene-13-hydroxy-midecamycin (iso-midecamycin), demycarosyl-midecamycin and iso-demycarosyl-midecamycin. In addition, 9-propionyl-josamycin shows 50% decomposition in contact with said 1st solution for about 25 minutes to give josamycin, isojosamycin, demycarosyl-josamycin, iso-demycarosyl-josamycin and 9-propionyl-decamyrosyljosamycin. Furthermore, josamycin (leucomycin $A_3$) is also decomposed rapidly in contact with said 1st solution to produce iso-josamycin, demycarosyl-josamycin and iso-demycarosyl-josamycin. From these facts, it can be presumed that there also occurs similar decomposition in oral preparations of 16-membered ring macrolide antibiotics in the gastric juice after oral administration.

The present inventors have performed intensive studies to prevent 16-membered ring macrolide antibiotics from such decomposition in an aqueous solution at an acidic region. As a result, it has been found quite unexpectedly that the 16-membered ring macrolide antibiotics can be well prevented from decomposition due to the allyl rearrangement reaction or demycarose reaction and that the 16-membered ring macrolide antibiotics can be stabilized by adding stabilizers which have buffering or antacid action and show pH 3–10 in an aqueous solution, e.g. neutral amino acids or their basic salts, acidic amino acid monobasic salts, basic amino acids, monobasic organic carboxylic acid salts, polybasic organic carboxylic acid salts, basic salts of uronic acid and inorganic salt antacids. However, 16-membered ring macrolide antibiotics have the disadvantage that bioavailability of the formulation of their oral preparations is decreased because they are insoluble until the antibiotics precipitate, although it is stabilized, in the neutral to alkaline region. Generally, pharmaceutical compounds soluble slightly in water and unstable in an acidic region tend to decompose in the gastric juice and cause to decrease in bioavailability if improved in solubility by fine pulverization [Am. J. Pharm., 135, 78 (1963)]. One of known methods for improvement of bioavailability is to suppress the decomposition of pharmaceutical compounds in the gastric juice by making them in the form of derivatives to reduce their solubility in the juice, and at the same time to make use of the difference between partition coefficients by making them in the form of derivatives [Chem. Pharm. Bull., 11, 1099 (1962)]. Another method for improving bioavailability of 14-membered ring macrolide antibiotics, for example erythromycin, is to use in the form of enteric coated preparations in order to inhibit the dissolution in the gastric juice and to allow them to dissolve in a part lower than the duodenum.

The present inventors have studied elution rates involved in the absorbability of basic 16-membered ring macrolide antibiotics such as midecamycin, josamycin, 3"-propionylleucomycin $A_5$, 9-propyljosamycin and 9,3"-diacetylmidecamycin. As a result, these 16-membered ring macrolide antibiotics have elution rates of only less than 15% in a physiological saline solution and such rates of only less than about 50% in a pH 4–5 weak acidic aqueous solution. Especially, 9,3"-diacetyl-midecamycin shows elution rate of only less than 10% even in a pH 4–5 weak acidic aqueous solution. However, 16-membered ring macrolide antibiotics have good elution rate of more than 95% in a pH 1.2–3 acidic aqueous solution except 9,3"-diacetylmidecamycin, although unstable in the acidic region as described above. In addition, 9,3"-diacetylmidecamycin also has good elution rate of more than 95% in a pH 1.2–2.5 acidic aqueous solution. From these results, it is found that these 16-membered ring macrolide antibiotics show a rapid reduction in solubility in the medium around pH 4–5 and have reduced bioavailability. Further studies reveal that good oral preparations of these 16-membered ring macrolide antibiotics with much decreased individual differences and improved bioavailability can be obtained without impairing their stability by adding such dissolution accelerators as substances which show pH 2.5–4 in an aqueous solution, i.e., monobasic organic carboxylic acids, polybasic organic carboxylic acids or their acidic monobasic salts or acidic polybasic inorganic acid monobasic salts, to the compositions of stable preparations with inhibited decomposition containing such 16-membered ring macrolide antibiotic and stabilizers which show pH 3–10 in aqueous solutions.

Furthermore, the present inventors have found that good oral preparations with more stabilized power of 16-membered ring macrolide antibiotics can be obtained by using dissolution accelerators coated by publicly known methods, for example by a microcapsulation technique using film-forming substances.

The present invention is based on the above findings, and relates to a stable 16-membered ring macrolide antibiotic oral preparation in which at least one kind of stabilizers which has pH 3–10 in an aqueous solution is contained in the 16-membered ring macrolide antibiotic oral preparation, and to an oral preparation in which a dissolution accelerator showing pH 2.5–4 in an aqueous solution is further contained. Furthermore, the present invention relates to a method for stabilization of the 16-membered ring macrolide antibiotic in an acidic aqueous solution, in which at least one kind of stabilizers which has pH 3–10 in an aqueous solution is added to the 16-membered ring macrolide antibiotics.

An object of the present invention is to provide stabilization of 16-membered ring macrolide antibiotics in the oral preparation and their stabilized preparations, and further to provide such stabilized preparations with little individual differences and good bioavailability.

In the accompanying drawings,

FIG. 17 shows a curve of stabilization of TMS-19-Q attained by the addition of calcium phosphate.

FIG. 18 shows a curve of stabilization of TMS-19-Q attained by the addition of trisodium citrate.

FIG. 19 shows a curve of stabilization of TMS-19-Q attained by the addition of monosodium L-asparaginate.

FIG. 20 shows a curve of stabilization of TMS-19-Q attained by the addition of monosodium L-glutamate.

FIG. 21 shows a change in stability of 9,3''-diacetyl midecamycin in a lapse of time, change in formation ratio of the components formed as the result of decomposition of 9,3''-diacetyl midecamycin and a curve of stabilization of 9,3''-diacetyl midecamycin attained by the addition of glycine.

FIG. 22 shows a curve of stabilization of 9,3''-diacetyl midecamycin attained by the addition of calcium phosphate.

FIG. 23 shows a curve of stabilization of 9,3''-diacetyl midecamycin attained by the addition of trisodium citrate.

FIG. 24 shows a curve of stabilization of 9,3''-diacetyl midecamycin attained by the addition of monosodium L-asparaginate.

FIG. 27 shows a curve of elution of TMS-19-Q against an amount of citric acid.

FIG. 28 shows a curve of elution of TMS-19-Q against an amount of tartaric acid.

Figure 2:
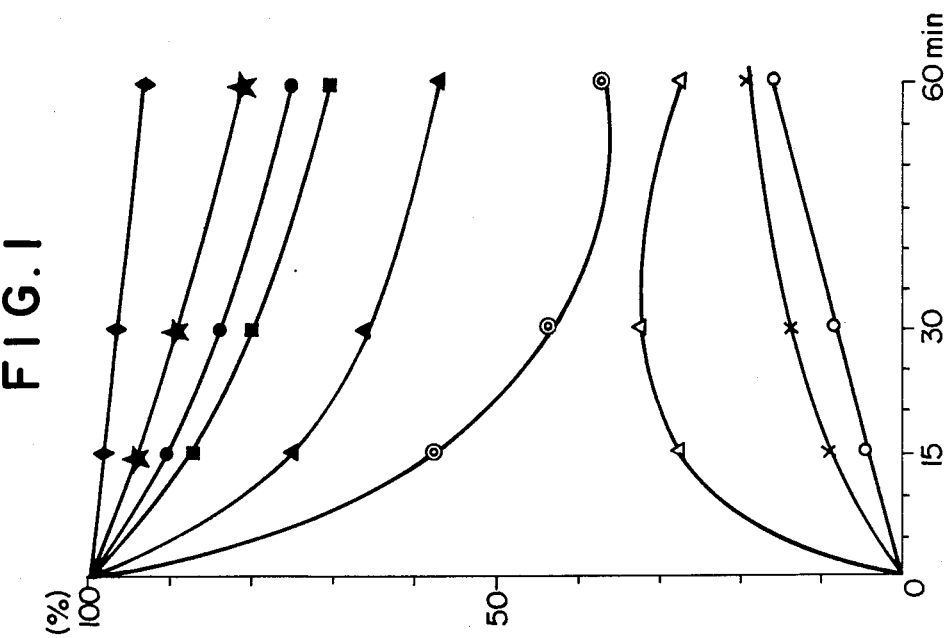
FIG. 2 represents a curve of stabilization of midecamycin by the addition of calcium phosphate.

Sixteen-membered ring macrolide antibiotics used as the object of the invention include 9-hydroxy 16-membered ring macrolide antibiotics at least having intramolecular 9-hydroxy-10,12-dieno groups, 9-acyloxy 16-membered ring macrolide antibiotics at least having intramolecular 9-acyloxy-10,12-dieno groups and 16-membered ring macrolide antibiotics having at least basic sugars, for example, mycaminose, as well as neutral sugars, for example, mycarose which are combined together by intramolecular ether-bonding. These 9-hydroxy 16-membered ring macrolide antibiotics become objects for the prevention of 9-deoxy-10,12-dedieno-9,11-diene-13-hydroxylation, i.e. conversion into isoform, due to allyl rearrangement reaction in the acidic region. In addition, the 9-acyloxy 16-membered ring macrolide antibiotics become objects for the prevention of iso conversion of 9-hydroxy 16-membered ring macrolide antibiotics formed by 9-deacylation in the acidic region. Furthermore, the 16-membered ring macrolide antibiotics having a mycarose group become objects for the prevention of decomposition into demycarosyl 16-membered ring macrolide antibiotics due to demycarose reaction in the acidic region. Sixteen-membered ring macrolide antibiotics having both hydroxy group and acyloxy group at 9-position can be used as objects for giving both of the effects of preventing iso conversion and decomposition into demycarosyl 16-membered macrolide antibiotics. Since before there have been known various kinds of 16membered ring macrolide antibiotics [see, for example 'The Outline of Antibiotics' the 2nd edition, pp.124–133, published by Tokyo University Publishing Association in April 1977]. As most preferable objects of the present invention there are represented mycarose group-containing 9-hydroxy or 9-acyloxy 16-membered ring macrolide antibiotics by the following general formula [I], but the invention is not limited to these compounds.

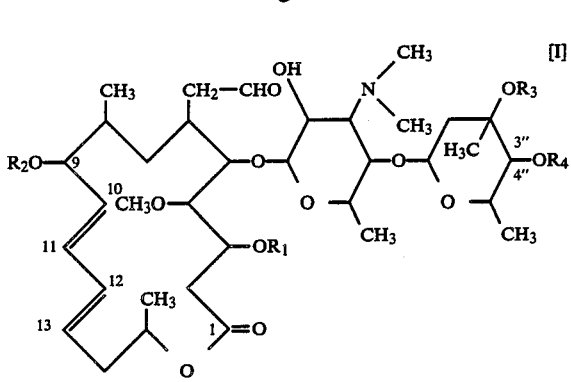

The substituents $R_1$, $R_2$, $R_3$ and $R_4$ in the structural formula of the basic 16-membered ring macrolide antibiotics indicated by the formula [I] are exemplified as follows: all of the $R_1$, $R_2$ and $R_3$ shows a hydrogen atom or a lower alkanoyl group; $R_4$ indicates a lower alkanoyl group; however, the substituents is not restricted by these examples.

| 16-membered ring macrolide antibiotics | $R_1$ | $R_2$ | $R_3$ | $R_4$ |
|---|---|---|---|---|
| leucomycin $A_1$ | —H | —H | —H | —COCH$_2$CH(CH$_3$)$_2$ |
| leucomycin $A_3$ | —COCH$_3$ | —H | —H | —COCH$_2$CH(CH$_3$)$_2$ |
| josamycin | —COCH$_3$ | —H | —H | —COCH$_2$CH(CH$_3$)$_2$ |
| YL-704A$_4$ | —COCH$_3$ | —H | —H | —COCH$_2$CH(CH$_3$)$_2$ |
| leucomycin $A_4$ | —COCH$_3$ | —H | —H | —COCH$_2$CH$_2$CH$_3$ |
| leucomycin $A_5$ | —H | —H | —H | —COCH$_2$CH$_2$CH$_3$ |
| leucomycin $A_6$ | —COCH$_3$ | —H | —H | —COCH$_2$CH$_3$ |
| YL-704B$_3$ | —COCH$_3$ | —H | —H | —COCH$_2$CH$_3$ |
| leucomycin $A_7$ | —H | —H | —H | —COCH$_2$CH$_3$ |
| leucomycin $A_8$ | —COCH$_3$ | —H | —H | —COCH$_3$ |
| leucomycin $A_9$ | —H | —H | —H | —COCH$_3$ |
| YL-704A$_1$ | —COCH$_2$CH$_3$ | —H | —H | —COCH$_2$CH(CH$_3$)$_2$ |
| SF-837A$_2$ | —COCH$_2$CH$_3$ | —H | —H | —COCH$_2$CH$_2$CH$_3$ |
| espinomycin $A_2$ | —COCH$_2$CH$_3$ | —H | —H | —COCH(CH$_3$)$_2$ |
| SF-837 (=SF-837A$_1$) | —COCH$_2$CH$_3$ | —H | —H | —COCH$_2$CH$_3$ |
| YL-704B$_2$ | —COCH$_2$CH$_3$ | —H | —H | —COCH$_2$CH$_3$ |
| espinomycin $A_1$ | —COCH$_2$CH$_3$ | —H | —H | —COCH$_2$CH$_3$ |
| Yl-704C$_2$ | —COCH$_2$CH$_3$ | —H | —H | —COCH$_3$ |
| espinomycin $A_3$ | —COCH$_2$CH$_3$ | —H | —H | —COCH$_3$ |
| 9-propionyljosamycin (9-propionylleucomycin $A_3$) | —COCH$_3$ | CH$_3$CH$_2$CO— | —H | —COCH$_2$CH(CH$_3$)$_2$ |
| 9,3''-diacetyl-SF-837 | —COCH$_2$CH$_3$ | CH$_3$CO— | CH$_3$CO— | —COCH$_2$CH$_3$ |
| 3''-propionylleucomycin $A_5$ | —H | —H | CH$_3$CH$_2$CO— | —COCH$_2$CH$_2$CH$_3$ |
| 9-acetylleucomycin $A_5$ | H— | CH$_3$CO | H— | —COCH$_2$CH$_2$CH$_3$ |
| 9-propionylleucomycin $A_5$ | H— | CH$_3$CH$_2$CO— | H— | —COCH$_2$CH$_2$CH$_3$ |
| 3''-acetylleucomycin $A_5$ | H— | H— | CH$_3$CO— | —COCH$_2$CH$_2$CH$_3$ |

-continued

| 16-membered ring macrolide antibiotics | R₁ | R₂ | R₃ | R₄ |
|---|---|---|---|---|
| 9,3″-diacetylleucomycin A₅ | H— | CH₃CO— | CH₃CO— | —COCH₂CH₂CH₃ |
| 9-propionyl-3″-acetylleucomycin A₅ | H— | CH₃CH₂CO— | CH₃CO— | —COCH₂CH₂CH₃ |
| 9-acetyl-3″-propionylleucomycin A₅ | H— | CH₃CO— | CH₃CH₂CO— | —COCH₂CH₂CH₃ |
| 9,3″-dipropionylleucomycin A₅ | H— | CH₃CH₂CO— | CH₃CH₂CO— | —COCH₂CH₂CH₃ |
| 3″-butylylleucomycin A₅ | H— | H— | CH₃CH₂CH₂CO— | —COCH₂CH₂CH₃ |
| 9-acetyl-3″-butylylleucomycin A₅ | H— | CH₃CO— | CH₃CH₂CH₂CO— | —COCH₂CH₂CH₃ |
| 9-propionyl-3″-butylylleucomycin A₅ | H— | CH₃CH₂CO— | CH₃CH₂CH₂CO— | —COCH₂CH₂CH₃ |
| 9-acetylleucomycin A₃ | —COCH₃ | CH₃CO— | —H | —COCH₂CH(CH₃)₂ |
| 3″-acetylleucomycin A₃ | —COCH₃ | —H | CH₃CO— | —COCH₂CH(CH₃)₂ |
| 9,3″-diacetylleucomycin A₃ | —COCH₃ | CH₃CO— | CH₃CO— | —COCH₂CH(CH₃)₂ |
| 3″-propionylleucomycin A₃ | —COCH₃ | —H | CH₃CH₂CO— | —COCH₂CH(CH₃)₂ |
| 9-acetyl-3″-propionylleucomycin A₃ | —COCH₃ | CH₃CO— | CH₃CH₂CO— | —COCH₂CH(CH₃)₂ |
| 9,3″-dipropynylleucomycin A₃ | —COCH₃ | CH₃CH₂CO— | CH₃CH₂CO— | —COCH₂CH(CH₃)₂ |
| 9-acetyl-3″-butylleucomycin A₃ | —COCH₃ | CH₃CO— | CH₃CH₂CH₂CO— | —COCH₂CH(CH₃)₂ |
| 9-propionyl-3″-butylylleucomycin A₃ | —COCH₃ | CH₃CH₂CO— | CH₃CH₂CH₂CO— | —COCH₂CH(CH₃)₂ |

The 16-membered ring macrolide antibiotics listed above are examples of compounds preferable as the object. In addition to these compounds, the above-described mycarose group-containing 16-membered ring macrolide antibiotics also include compounds represented by the structural formula of [I] whose partial structure of R₂O-group in the 9-position is changed into a carbonyl group, and compounds having an epoxy group in place of the double bond between the 12- and 13-positions of the formula [I]. Moreover, the objects of the invention include derivatives obtained by chemically treating the formyl of the substituent —CH₂CHO in the 16-membered ring aglycone of 16-membered ring macrolide antibiotics represented by the general formula [I], and various basic 16-membered ring macrolide antibiotics having sugar substituents in the aglycon.

The stabilizers showing pH 3-10 used in the invention may be substances having a buffering or antacid action and showing pH 3-10, preferably 5.5-6.5. These are, for example, neutral amino acids or their basic salts, basic salts of acidic amino acids, basic amino acids, basic salts of organic carboxylic acids, basic salts of polybasic organic carboxylic acids, basic salts of uronic acid or inorganic salt antacids. The neutral amino acids or basic salts thereof include glycine, alanine, aminobutyric acid, proline, leucine, isoleucine, methionine, threonine, serine, valine, or their aluminium salts, for example aluminium glycinate. Among these, glycine, alanine and aluminium glycinate, both of which show pH 5.5-6.5, are preferable. The basic salts of acidic amino acid include monobasic salts such as a monosodium, monopotassium or magnesium salt of glutaminic or aspartic acid. Among these monobasic salts, monosodium glutamate or monosodium aspartate is preferable. The basic amino acids include arginine, glutamine, asparagine, citrulin, tryptophane and histidine. Especially, histidine is preferable. The basic salts of monobasic organic carboxylic acid include basic salts such as sodium, potassium, magnesium or aluminium salts of saturated monobasic organic carboxylic acids such as acetic acid and propionic acid, of unsaturated monobasic organic acids such as acrylic acid, crotonic acid and vinylacetic acid, and of other monobasic organic acids such as lactic acid, pyruvic acid, glyceric acid and acetoacetic acid. The basic salts of polybasic organic carboxylic acid include mono-, di- or tri-sodium, potassium, magnesium, calcium or aluminium salts of saturated polybasic organic carboxylic acids such as oxalic acid, malonic acid, succinic acid, glutaric acid, adipic acid and pimelic acid, of unsaturated polybasic organic carboxylic acids such as maleic acid and fumaric acid, and of other polybasic organic carboxylic acids such as meso-oxalic acid, malic acid, oxalacetic acid and citric acid. Among these, trisodium citrate is preferable. The basic salts of uric acids include sodium salts of glucuronic acid, galacturonic acid or their polymers such as alginic acid or peptic acid and dihydroxyaluminium aminoacetate sodium alginate. The inorganic salt antacids include calcium hydrogenphosphate, disodium hydrogenphosphate, dipotassium hydrogenphosphate, magnesium hydrogenphosphate, calcium carbonate, sodium carbonate, potassium carbonate, sodium hydrogen carbonate, aluminium carbonate, magnesium carbonate, potassium metasilicate, magnesium aluminate metasilicate, sodium metasilicate, synthetic aluminium silicate, magnesium silicate, aluminium silicate, magnesium aluminate silicate, magnesium-bismuth aluminate silicate, magnesium oxide, alumina-magnesium hydroxide, magnesium peroxide, magnesium hydroxide, aluminium hydroxide, synthetic hydrotarphite, aluminium phosphate and others. Especially, calcium phosphate and magnesium phosphate are preferable. Each of these stabilizers may be used alone or in the form of a mixture. The stabilizers showing pH 3–10 in an aqueous solution need to be used in more than 10 mg, preferably more than 50 mg, per 100 mg potency of the 16-membered ring macrolide antibiotics and in an amount of 100–1000 mg when formulated. A method for stabilization of 16-membered ring macrolide antibiotics of the present invention will be described in detail. The afore-mentioned various 16-membered ring macrolide antibiotics, for example 9-hydroxy 16-membered ring macrolides such as midecamycin, 3″-propionyl-leucomycin A$_5$ and josamycin and 9-acyloxy 16-membered ring macrolides such as 9,3″-diacetylmidecamycin and 9-propionyljosamycin show extremely poor residual rates when added to an acidic solution of the Japanese Pharmacopoeia 1st liquid (pH 1.2) and allowed to stand. That is, the 9hydroxy 16-membered ring maclorides decompose in a short time to by-produce their iso, demycarosyl and/or isodemycarosyl forms. The 9-acyloxy 16-membered ring macrolides decompose, too, to by-produce their 9-deacyl, 9-deacyl-iso, demycarosyl, 9-deacyl-demycarosyl or 9-deacyl-iso-demycarosyl forms. Their stability is improved simply by adding an adequate amount of the stabilizers showing pH 3–10 in an aqueous solution, to acidic solutions used in advance. For example, when acidic solutions used is at pH 1.2, 16 membered ring macrolide antibiotics used can remain stably in approximately more than 70% by adding the stabilizers to around pH 2, in approximately more than 80% by adding them to around pH 2.5, and in approximately more than 90% to around pH 3. Thus, the use of the stabilizers in excess makes no harm to their stabilization. The adequate amount of the stabilizers used can be determined, depending on desired rates of stabilization. From these reasons, also in their formulation, the amount of the stabilizers used can be adequately determined depending on desired rates of stabilization, and is not particularly limited. For example, in oral preparation of the 16-membered ring macrolide antibiotics, especially 50-mg potency tablets for one tablet a time administration, the stabilizers are allowed to be contained in an amount of more than 150 mg, preferably 200–1000 mg, per tablet. In 100 mg-potency tablets for two tablets a time administration, the stabilizers are allowed to be contained in an amount of more than 50 mg, preferably 150–500 mg, per tablet. In 200 mg-potency tablets for one tablet a time administration, the stabilizers are allowed to be contained in an amount of more than 150 mg, preferably 200–1000 mg, per tablet. In 200 mg-potency tablets for two tablets a time administration, the stabilizers are allowed to be contained in an amount of more than 50 mg, preferably 150–500 mg, per tablet. Thus, preparations are designed to contain the stabilizers in a total amount of more than 100 mg, preferably 150–1000 mg, per administration. Moreover, these amounts of stabilizers used are only examples, and do not inhibit the use of larger amounts. Also in the design of oral preparations such as powder, fine granules, capsules, granules and dry syrups, their amounts equal or in excess to the above-described ones are allowed to be contained.

In these 16-membered ring macrolide antibiotic oral preparations, further, there are allowed to be improved not only the stability of 16-membered ring macrolides, but also their bioavailability preferably under the conditions of stabilization by elevating their absorbability. For this purpose, there are used dissolution accelerators showing pH 2.5–4 in an aqueous solution as additives. The dissolution accelerators showing pH 2.5–4 in an aqueous solution include monobasic organic carboxylic acids, polybasic organic carboxylic acids or their acidic monobasic salts thereof and monobasic salts of acidic polybasic inorganic acids. More particularly, the monobasic organic carboxylic acids include saturated organic carboxylic acids such as acetic acid and propionic acid, unsaturated organic carboxylic acids such as acrylic acid, crotonic acid and vinylacetic acid and hydroxy- or carbonyl-carboxylic acids such as lactic acid, pyruvic acid, glyceric acid and acetoacetic acid. The polybasic organic carboxylic acids or their acidic monobasic salts include saturated polybasic organic carboxylic acids such as oxalic acid, malonic acid, succinic acid, glutaric acid, adipic acid and pimelic acid, unsaturated polybasic organic carboxylic acids such as maleic acid and fumaric acid, hydroxy- or carbonyl-polybasic organic carboxylic acids such as tartaric acid, malic acid, meso-oxalic acid, oxalacetic acid and citric acid, and monobasic salts such as monosodium citrate and monopotassium citrate. The monobasic salts of acidic polybasic inorganic acid include sodium dihydrogenphosphate and potassium dihydrogenphosphate. They may be used alone or in the form of a mixture. These dissolution accelerators preferably show pH 3–4 in an aqueous solution. Tartaric acid, citric acid, monosodium citrate and sodium dihydrogen phosphate are preferred.

An amount of the dissolution accelerators used, showing pH 2.5–4 in an aqueous solution will be described in detail. To beagles are orally administered 5 tablets which contain a 100 mg potency of 3″-propionylleucomycin A$_5$ as the base, 170 mg of glycine as a stabilizer and 0 mg, i.g. no addition, 10 mg, 20 mg, 30 mg or 40 mg, respectively, of citric acid as a dissolution accelerator. As a result, the tablets have AUC (area under a blood level versus time curve) of 11.8 μg potency.hr/ml with 0 mg of citric acid, 12.3 μg potency.hr/ml with 10 mg, 17.0 μg potency.hr/ml with 20 mg, 20.5 μg potency.hr/ml with 30 mg and 20.9 μg potency.hr/ml with 40 mg. Good blood concentrations or absorbability is performed with a citric acid amount of more than 30 mg per tablet. In the medium of 40 ml physiological saline solution with 120 ml water added, a mixture of 3″-propionylleucomycin A$_5$ (200 mg potency) and glycine (340 mg) shows pH 5.87 as determined under no addition of citric acid, pH 5.51 under 10 mg citric acid, and pH 5.18 under 20 mg. In all of these cases, the elution rate of 3″-propionylleucomycin A$_5$ is less than 60%. In contrast, the mixture shows pH 4.35 under the addition of 40 mg citric acid, pH 4.10 under 60 mg and pH 3.95 under 80 mg, indicating that the elution rate is more than 95% under the addition of 40 mg or more of citric acid. In order to obtain their good absorbability, generally, it is necessary to use the pH at which the elution rate is favorable. Therefore, the amount of dissolution accelerators need to be determined so that the pH shows approximately 4-3.5 under their addition. From these reasons, the absorbability of the 16-membered ring macrolide antibiotics can be improved by using the dissolution accelerators in an amount of 5 mg or more, preferably 10–400 mg, per 100 mg potency of the antibiotics. The accelerators need to be used in 5–100 mg in formulating preparations. It is particularly preferred that these dissolution accelerators, for example tartaric acid and citric acid are used in a total amount of 40–100 mg at single administration. That is, one tablet is allowed to contain about 40–100 mg in the administration of one tablet a time, and about 20–50 mg each in two tablets a time. It is also particularly preferred, when the antibiotics are applied orally in the form of powders, fine granules, capsules, granules or dry syrups, that the accelerators are used in approximately 40–100 mg to the 16-membered ring macrolide antibiotics given in a 200 mg potency a time. It is suitable for preservation that these dissolution accelerators are used coated with film-forming substances by a microcapsulization technique using the accelerators as core materials.

In coating these dissolution accelerators, usable film-forming substances need to be non-toxic to the living body and dissolvable or decomposable in vivo, or capable of releasing the accelerators by their semipermeability. These film-forming substances include macromolecular substances such as alkyl celluloses (e.g. ethyl cellulose and propyl cellulose), cellulose acetate, cellulose propionate, Eudragit RS ®, Eudragit RL ®, hydroxymethyl cellulose, hydroxyethyl cellulose and hydroxypropyl cellulose. Among these, ethyl cellulose is preferable. The dissolution accelerators coated with film-forming substances are obtained by preparing uniform solutions of film-forming substances using solvents dissolving the substances, by adding, to these, dissolution accelerators as core materials, and then by adding these solutions in liquid-drop form to capsulization media to desolvent. This techique is often used usually for microcapsulization, and divided into phase separation, in-liquid hardening coating and in-liquid drying processes, depending upon solvents and capsulization media used and requirements for desolventing. For example, there may be used a microcapsulization process by in-liquid drying, which comprises dissolving film-forming substances in media such as methanol, ethanol and acetone, adding, to these, dissolution accelerators as core materials, emulsion dispersing these mixtures in silicon oil or liquid paraffin, and then removing the solvents to coat the dissolution accelerators as core materials. As another coating process, for example, there may be also used a phase separation means which comprises dissolving film-forming substances in warmed cyclohexane, and precipitating these under cooling to coat the surface of dissolution accelerators added as core materials, making use of their solubility differences between under warming and cooling. In addition, based on publicly known various microcapsulization methods, there can be used a process utilizing about 10–500 μ particles of dissolution accelerators as core materials. In the dissolution accelerators coated with film-forming substances used in the present invention, the ratio of the accelerators to film-forming substances is about 1:0.5–9, preferably about 1:1–5, by parts by wt. The dissolution accelerators coated with film-forming substances can be determined for their amounts used on the basis of the amount of the accelerators contained. When used in formulating preparations, such coated dissolution accelerators can keep stable the 16-membered ring macrolide antibiotics over a longer period of time compared to uncoated accelerators.

In order to obtain the desired stable 16-membered ring macrolide antibiotics oral preparations, there can be used publicly known techniques for conventional oral preparations such as tablets, powders, fine granules, capsules, granules and dry syrups. In preparing tablets by a dry or wet process, for example, a given amount of the above-described stabilizers, dissolution accelerators or coated dissolution accelerators are added to a given amount of the 16-membered ring macrolide antibiotics, together with vehicles such as lactose, purified sucrose, glucose, starch and microcrystalline cellulose, disintegrators such as calcium carbonate and starch, lubricants such as magnesium stearate and calsium stearate, binders such as gum arabic, tragacanth, carboxymethylcellulose, hydroxypropylmethylcellulose and sodium alginate solutions, water for binding and ethanol. Generally, oral preparations for children are formulated to 50–100 mg potency per administration, and those for adults are formulated to 200–400 mg potency per administration. The oral preparations thus obtained can keep stably the 16-membered ring macrolide antibiotics even under acidic conditions in gastric juice, have markedly decreased individual differences and show excellent bioavailability.

The present invention is described concretely in the following examples, but these examples do not limit the scope of the 16-membered ring macrolide antibiotics and the kinds and amount of the stabilizers or dissolution accelerators usable in the invention.

EXAMPLE 1

Stabilization of midecamycin 200 mg of midecamycin was dissolved into 40 ml of Japan Pharmacopoeia lst solution (pH 1.2) cooled in an ice bath. On the occasion, 150–900 mg of glycine was added thereto as stabilizer (no glycine was used for the control). Then, after this solution was kept at a constant temperature in a thermostat whose temperature is maintained at 37° C., sampling of 3 ml thereof was conducted as a lapse of time (after 15 minutes, 30 minutes and 60 minutes). Then, pH of this solution was adjusted to be at 9-10 by adding 4 ml of 10% w/w aqueous solution of sodium carbonate to each solution and it was extracted three times with 10 ml of ethyl acetate each. The extracted solution was concentrated under reduced pressure and the residue was dissolved into 1 ml of chloroform. Then, 2 μl of the solution (about 30 μg in terms of weight) was charged onto a silicagel thin layer plate (Merck art. 5715) and was developed by using the developing solvents comprising chloroform, methanol, acetic acid and water at 79:7:7:1 and benzene, ethyl acetate and methanol at 11:4:1, respectively, and the relative ratio of the spot of midecamycin and those of the decomposites thereof separated on the thin layer plate was measured by a densitometer (wavelength of 232 nm was used).

Figure 1:
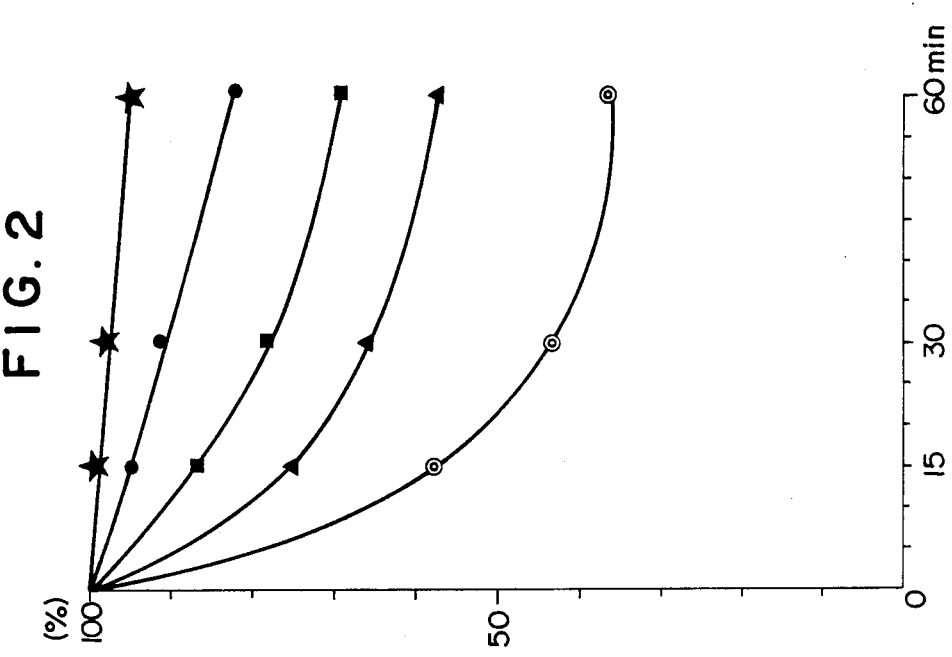
FIG. 1 shows the change in stability of midecamycin in a lapse of time, the change in formation ratio of the components which is formed as the result of decomposition of midecamycin and a curve of stabilization of midecamycin by the addition of glycine.

The results are as indicated in FIG. 1, wherein ⊚-⊚ indicates a curve of the changes in stability of midecamycin in a lapse of time as the control (in which no glycine was used); ▲-▲ indicates the formation ratio of 9-deoxy-10,12-dedieno-9,11-dien-13-hydroxy-midecamycin (iso-midecamycin); X-X indicates the formation ratio of demycarosyl-midecamycin which was generated as a lapse of time; and ○-○ indicates a curve of the formation ratio of 9-deoxy-10,12-dedieno-9,11-dien-13-hydroxy-demycarosyl-midecamycin (iso-demycarosyl-midecamycin).

As shown in FIG. 1, midecamycin is extremely unstable in the 1st solution which indicates a pH value equivalent to that of gastric juice. For example, the residual amount of midecamycin after the contact for 30 minutes with the 1st solution was only 45%, and the balacne of 55% became decomposites thereof, and after the contract for 60 minutes, the residual amount of midecamycin was 35% and the balance of 65% became decomposites thereof. When the similar procedures are followed by using midecamycin capsules, which are sold in the market, the results almost identical as those shown in FIG. 1 were obtained.

On the contrary, in case glycine is used, which is indicated as a stabilizer in the present invention, midecamycin gets stabilized well; in FIG. 1, ▲-▲ is a curve indicating how midecamycin was stabilized when 150 mg of glycine was used (at the time, the pH value was indicated to be 1.7); ■-■ a curve indicating how midecamycin gets stabilized when 300 mg of glycine was used (the pH value was 2.3); and a ●-● is a curve which shows the stability of midecamycin when 350 mg of glycine was used (the pH value was indicated to be 2.36); and further ★-★ is a curve which indicates how midecamycin gets when 400 mg of glycine was used (pH value was indicated to be 2.5); and ♦-♦ is a curve indicating the stability of midecamycin when 900 mg of glycine is used (pH value is 2.96).

Under the present invention, the stability attained when 150 mg of glycine was used (▲-▲) improved by 50% compared with the control (in terms of the value at 30 minutes), and by the use of a larger amount of glycine, stability of midecamycin was achieved to such a level that it gets hardly decomposed.

EXAMPLE 2

In place of glycine in Example 1 above, 150–400 mg of calcium phosphate was used hereunder to test stability of midecamycin in the same procedures as those applied in Example 1.

The results of such test are as shown in FIG. 2, wherein ⊚-⊚ indicates a curve of the changes in stability of midecamycin in a lapse of time as the control (in the case no calcium phosphate is used). In FIG. 2, ▲-▲ indicates a curve which shows the stability o attained when 150 mg of calcium phosphate was used (the pH value was indicated to be 1.69); and ■-■ is a curve which shows the stability of midecamycin a when 250 mg of calcium phosphate was used (the pH value was indicated to be 2.25); and ●-● is a curve which shows the stability of midecamycin attained when 300 mg of calcium phosphate was used (the pH value was indicated to be 2.69); and ★-★ represents a curve which shows the stability of midecamycin attained when 400 mg of calcium phosphate was used (the pH value was indicated to be 3.19).

The results herein indicate that midecamycin was extremely well stabilized by the use of calcium phosphate.

EXAMPLE 3

In place of glycine in Example 1, 150–300 mg of tri-sodium citrate was used hereunder to test stability of midecamycin in the same procedures as those applied in Example 1.

Figure 3:
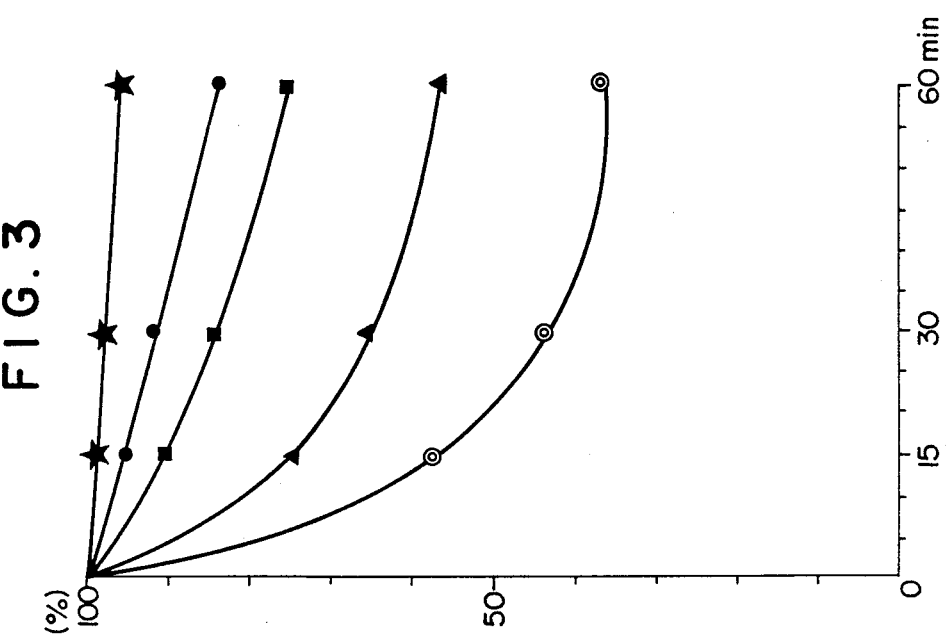
FIG. 3 represents a curve of stabilization of midecamycin by the addition of trisodium citrate.

The results of such test are as shown in FIG. 3, wherein ⊚-⊚ indicates a curve of the changes in stability of midecamycin in a lapse of time as the control (in the case no such sodium citrate was used) In FIG. 3, ▲-▲ indicates a curve which shows the stability of modecamycin attained when 150 mg of tri-sodium citrate was used (the pH value was indicated to be 1.67); and ■-■ is a curve which shows the stability of midecamycin attained when 225 mg of tri-sodium citrate was used (the pH value was indicated to be 2.36); and ●-● is a curve which shows the stability of midecamycin attained when 250 mg of tri-sodium citrate was used (the pH value was indicated to be 2.71); and ★-★ is a curve which shows the stability of midecamycin attained when 300 mg of tri-sodium citrate was used (the pH value was indicated to be 3.30).

The results herein indicate that midecamycin was extremely well stabilized by the use of tri-sodium citrate.

EXAMPLE 4

In place of glycine in Example 1 above, 200–500 mg of L-aspartic acid monosodium salt (hereinafter called Asp.Na) was used hereunder to test stability of midecamycin in the same procedures as those applied in Example 1.

Figure 4:
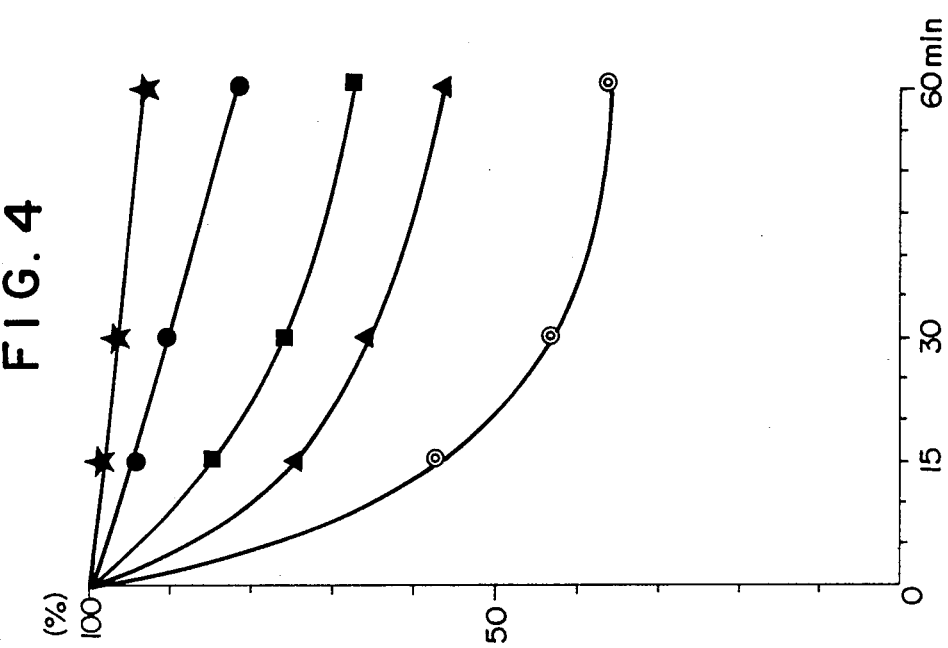
FIG. 4 represents a curve of stabilization of midecamycin by the addition of monosodium L-asparaginate.

The results of such test are as shown in FIG. 4, wherein ⊚-⊚ indicates a curve of the changes in stability of midecamycin in a lapse of time as the control (in the case no Asp.Na was used). In FIG. 4, ▲-▲ indicates a curve which shows the stability of midecamycin attained when 200 mg of Asp.Na was used (the pH value was 1.73); ■-■ is a curve which shows the stability of midecamycin attained when 300 mg of Asp.Na was used (the pH value was 2.16); ●-● is a curve which shows the stability of midecamycin attained when 400 mg of Asp.Na was used (the pH value was indicated to be 2.62); and ★-★ represents a curve which shows the stability of midecamycin attached when 500 mg of Asp.Na was used (the pH value was 3.02).

The results herein indicate that the stability of midecamycin was very much enhanced by the use of Asp.Na.

EXAMPLE 5

In place of glycine in Example 1, 200–500 mg of monosodium glutamate (hereinafter called "Glu.Na") was used hereunder to test stability of midecamycin in the same procedures as those applied in Example 1.

Figure 5:
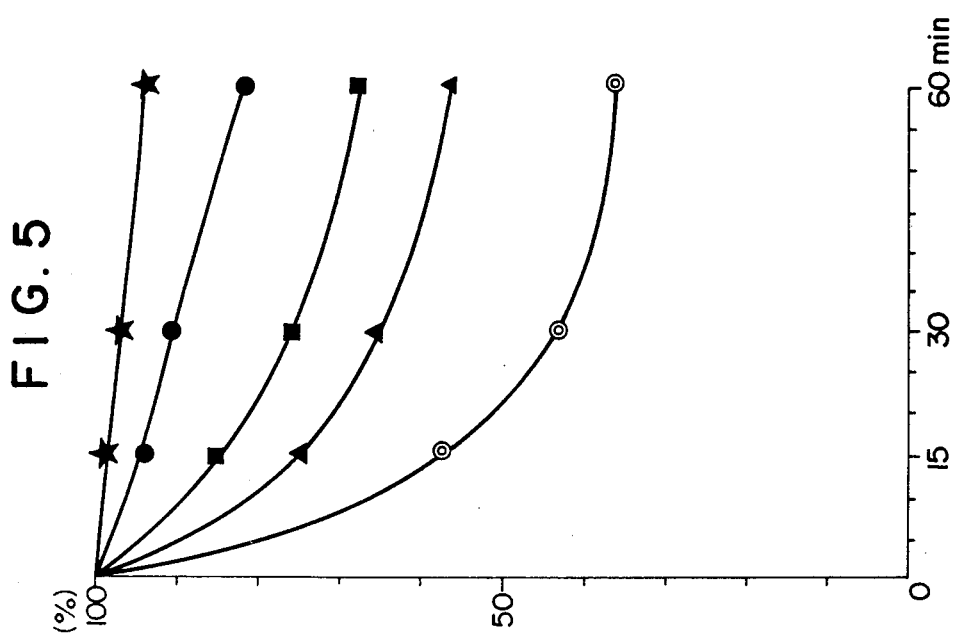
FIG. 5 represents a curve of stabilization of monosodium L-glutamate.

The results of such test are as shown in FIG. 5, wherein ⊚-⊚ indicates a curve of the changes in stability of midecamycin in a lapse of time as the control (in the case no Glu.Na was used). In FIG. 5, ▲-▲ indicates a curve which shows the stability of midecamycin attained when 200 mg of Glu.Na was used (the pH value was 1.70); and ■-■ is a curve which shows the stability of midecamycin attained when 300 mg of Glu.Na was used (the pH value was 2.16); ●-● is a curve which shows the stability of midecamycin attained when 400 mg of Glu.Na was used (the pH value was 2.65) and ★-★ is a curve which shows the stability of midecamycin attained when 500 mg of Glu.Na was used (the pH value was 3.15).

The results herein indicate that the stability of midecamycin was very much enhanced by the use of Glu.Na salt.

EXAMPLE 6

Stabilization of Josamycin 200 mg of josamycin was dissolved into 40 ml of Japan Pharmacopoeia 1st solution (pH 1.2) cooled in an ice bath. On the occasion, 150–900 mg glycine was added thereto as stabilizer (no glycine was used for the control). Then, after this solution was kept at a constant temperature in a thermostat whose temperature is maintained at 37° C., sampling of 3 ml thereof was conducted in a lapse of time (after 15 minutes, 30 minutes and 60 minutes). Then, pH of this solution was adjusted to be at 9–10 by adding to each solution 4 ml of 10% w/w aqueous solution of sodium carbonate and it was extracted three times with 10 ml of ethyl acetate each. The extracted solution was concentrated under reduced pressure and the residue was dissolved into 1 ml of chloroform. Then 2 μl of the solution (about 30 μg in terms of weight) was charged onto a silicagel thin layer plate (Merck art. 5715) and was developed by using the developing solvents comprising chloroform, methanol, acetic acid and water at the ratio of 79:7:7:1, and benzene, ethyl acetate and methanol at the ratio of 11:4:1, respectively, and the relative ratio of the spot of josamycin and those of the decomposites thereof separated on the thin layer plate was measured by a densitometer (wavelength of 232 nm was used).

Figure 6:
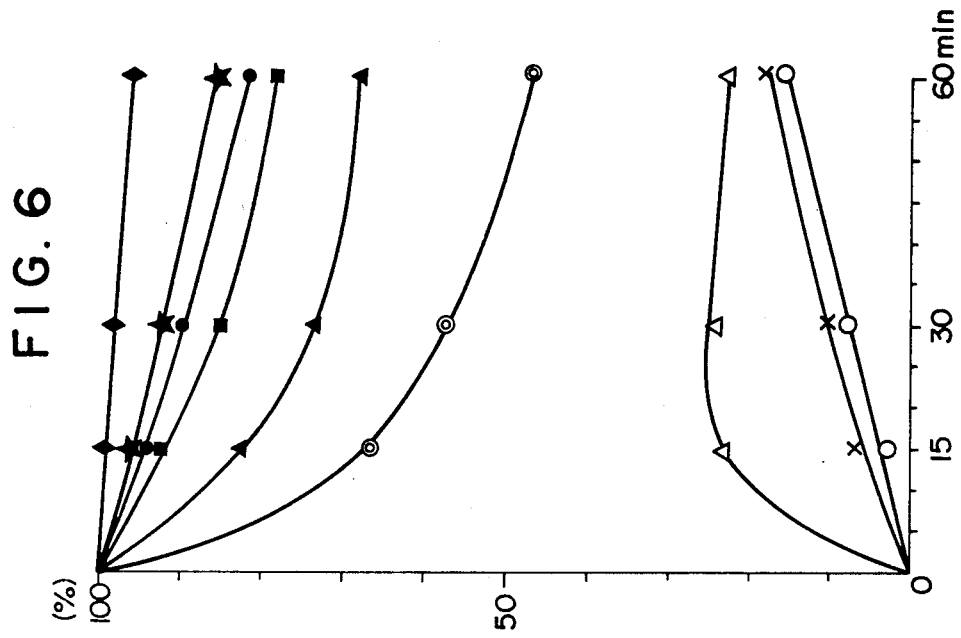
FIG. 6 shows the change in stability of josamycin in a lapse of time, change in formation ratio of the components which is as the result of decomposition of josamycin, and a curve of stabilization of josamycin attained by the addition of glycine.

The results are as indicated in FIG. 6, wherein ⊙-⊙ indicates a curve of the changes in stability of josamycin in a lapse of time as the control (in which no glycine was used); △-△ indicates the formation ratio of 9-deoxy-10,12-dedieno-9,11-dien-13-hydroxy-josamycin (iso-josamycin); X-X indicates the formation ratio of demycarosyl-josamycin which was generated in a lapse of time; and ○-○ indicates a curve of the formation ratio of 9-deoxy-10,12-dedieno-9,11-dien-13-hydroxy-demycarosyl-josamycin (isodemycarosyl-josamycin).

As shown in FIG. 6, josamycin is extremely unstable in the 1st solution which indicates a pH value equivalent to that of gastric juice. For example, the residual amount of midecamycin 30 minutes after the contact with the 1st solution became only 57.4%, and the balance of 42.6% was decomposites thereof, and 60 minites after the contact, the residual amount of josamycin was 46.7% and the balance of 53.3% became decomposites thereof. When the similar procedures were followed by using a josamycin tablet which were sold in the market, the results almost identical as those shown in FIG. 6 were obtained.

On the contrary, in case glycine was used, which is indicated as a stabilizer in the present invention, josamycin was stabilized well; in FIG. 6, ▲-▲ is a curve indicating the stability of josamycin attained when 150 mg of glycine was used (at the time, the pH value was 1.7); ■-■ is a curve indicating the stability of josamycin attained when 300 mg of glycine was used (the pH value was 2.25); ●-● is a curve which shows the stability of josamycin attained when 350 mg of glycine was used (the pH value was 2.36); -★ is a curve which indicates the stability of josamycin attained when 400 mg of glycine was used (pH value was 2.5); and ◆-◆ is a curve indicating the stability of josamycin when 900 mg of glycine was used (pH value was 2.96).

Under the present invention, the stability attained when 150 mg of glycine was used ( ▲-▲ ) improved by 30% compared with the control (in terms of the value at 30 minutes), and by the use of a larger amount of glycine, stability of josamycin was achieved to such a level that it was hardly decomposed.

EXAMPLE 7

In place of glycine in Example 6 above, 150–400 mg of calcium phosphate as a stabilizer was used hereunder to test stability of josamycin in the same procedures as those applied in Example 6.

Figure 7:
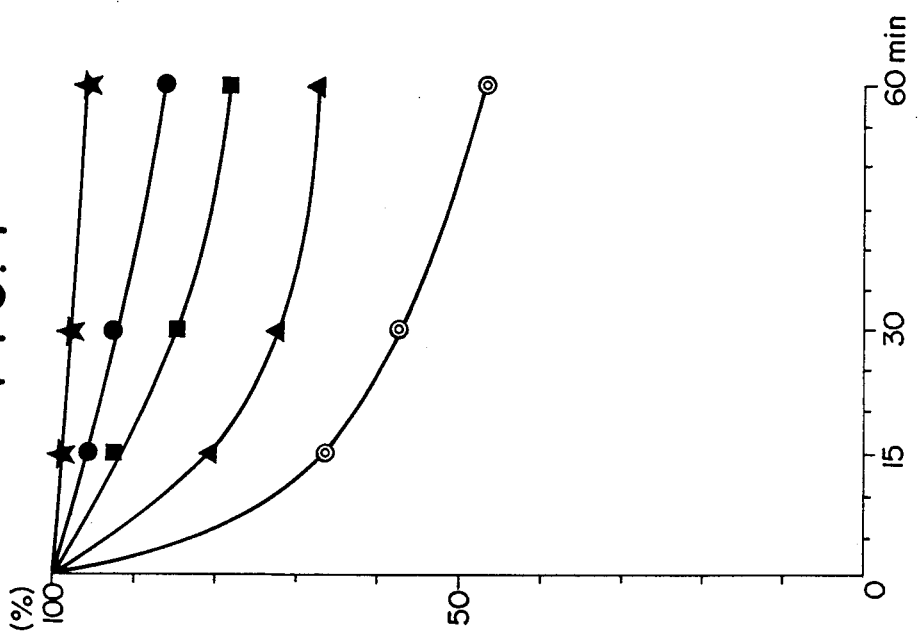
FIG. 7 shows a curve of stabilization of josamycin attained by the addition of calcium phosphate.

The results of such test are as shown in FIG. 7, wherein ⊙-⊙ indicates a curve of the changes in stability of josamycin in a lapse of time as the control (in the case no calcium phosphate was used). In FIG. 7, ▲-▲ indicates a curve which shows the stability of josamycin attained when 150 mg of calcium phosphate was used (the pH value was 1.69); and ■-■ is a curve which shows the stability of josamycin attained when 250 mg of calcium phosphate was used (the pH value was 2.25); and ●-● is a curve which shows the stability of josamycin attained when 300 mg of calcium phosphate was used (the pH value was 2.69); and ★-★ represents a curve which shows the stability of josamycin attained when 400 mg of calcium phosphate was used (the pH value was 3.18).

The results herein above indicated that the stability of josamycin was very much enhanced by the use of calcium phosphate.

EXAMPLE 8

In place of glycine in Example 6, 150–300 mg of tri-sodium citrate was used hereunder to test stability of josamycin in the same procedures as those applied in Example 6.

Figure 8:
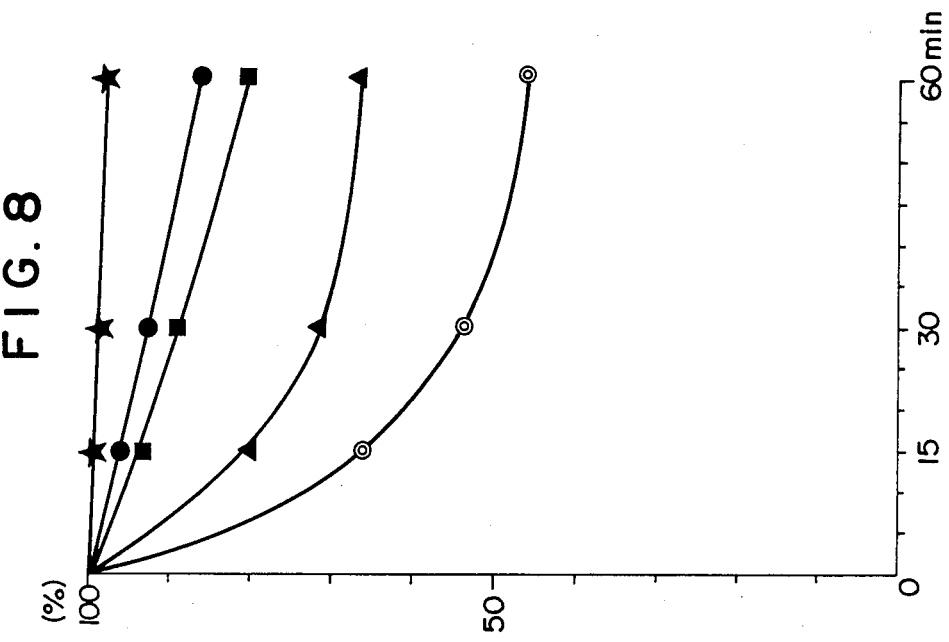
FIG. 8 shows a curve of stabilization of josamycin attained by the addition of trisodium citrate.

The results of such test are as shown in FIG. 8, wherein ⊙-⊙ indicates a curve of the changes in stability of josamycin in a lapse of time as the control (in the case no tri-sodium citrate was used). In FIG. 8, ▲-▲ indicates a curve which shows the stability of josamycin attained when 150 mg of tri-sodium citrate was used (the pH value was 1.68); and ■-■ is a curve which shows the stability of josamycin attained when 225 mg of tri-sodium citrate was used (the pH value was 2.35); and is a curve which shows the stability of josamycin attained when 250 mg of tri-sodium citrate was used (the pH value was 2.70); and ★-★ is a curve which shows the stability of josamycin attained when 300 mg of trisodium citrate salt was used (the pH value was 3.30).

The results herein indicate that the stability of josamycin was very much enhanced by the use of trisodium citrate.

EXAMPLE 9

In place of glycine in Example 6 above, 200–500 mg of Asp.Na was used hereunder to test stability of josamycin in the same procedures as those applied in Example 6

Figure 9:
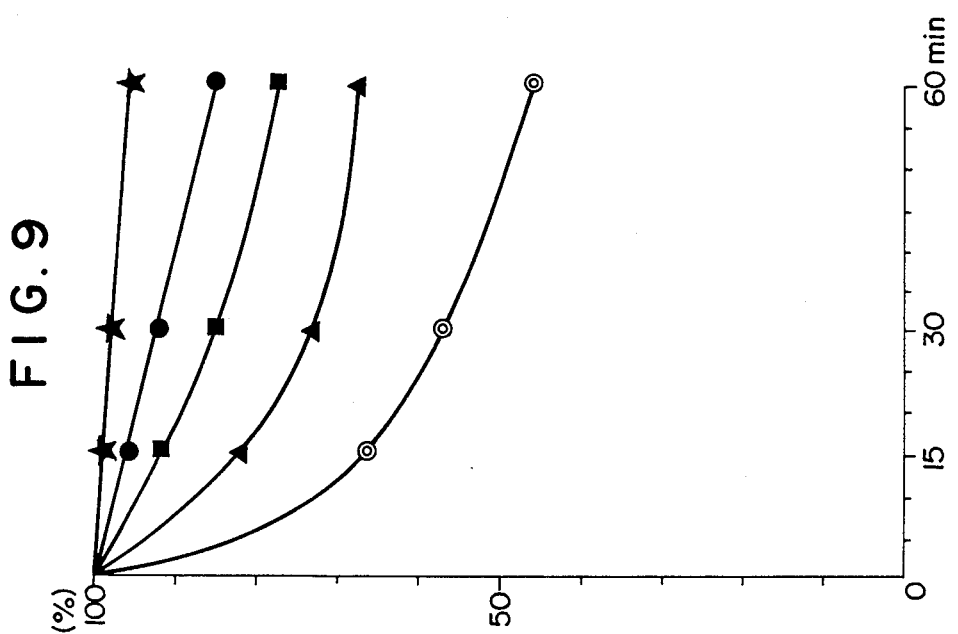
FIG. 9 shows curve of stabilization of josamycin attained by the addition of monosodium L-asparaginate.

The results of such test are as shown in FIG. 9, wherein ⊚-⊚ indicates a curve of the changes in stability of josamycin in a lapse of time as the control (in the case no Asp.Na was used). In FIG. 9, ▲-▲ indicates a curve which shows the stability of josamycin attained when 200 mg of Asp.Na was used (the pH value was 1.75); and ■-■ is a curve which shows the stability of josamycin attained when 300 mg of Asp.Na was used (the pH value was 2.16); and ●-● is a curve which shows the stability of josamycin attained when 400 mg of Asp.Na was used (the pH value was 2.62); and ★-★ represents a curve which shows the stability of josamycin attained when 500 mg of Asp.Na was used (the pH value was 3.02).

The results obtained herein indicate that the stability of josamycin was very much enhanced by the use of Asp.Na.

EXAMPLE 10

In place of glycine in Example 6, 200–500 mg of Glu.Na was used hereunder to test stability of josamycin in the same procedures as those applied in Example 6.

Figure 10:
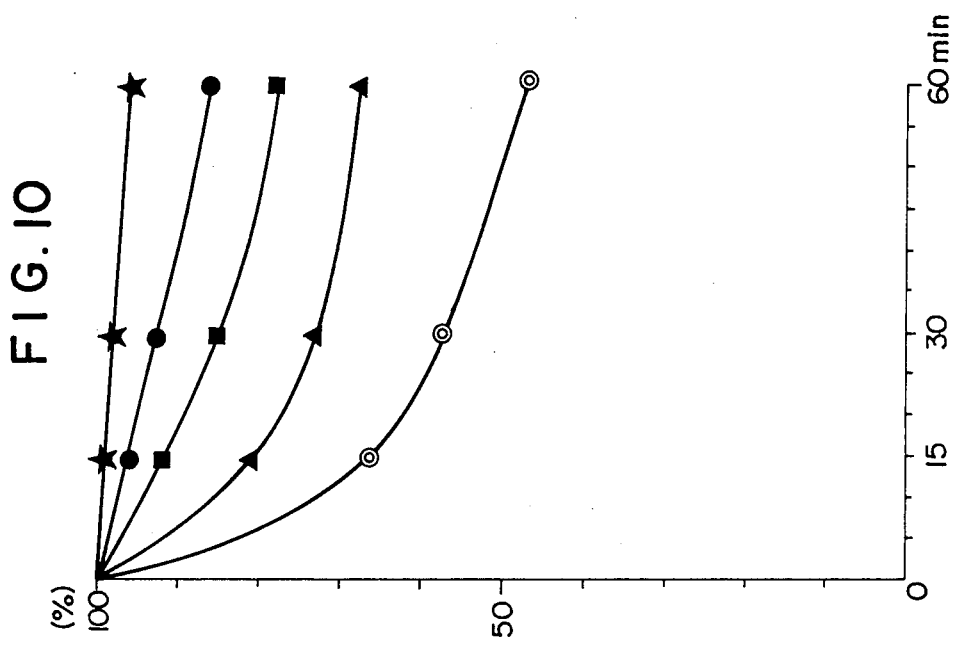
FIG. 10 shows a curve of stabilization of josamycin by the addition of monosodium L-glutamate.

The results of such test are as shown in FIG. 10, wherein ⊚-⊚ indicates a curve of the changes in stability of josamycin in a lapse of time as the control (in the case no Glu.Na was used). In FIG. 10, ▲-▲ indicates a curve which shows the stability of josamycin attained when 200 mg of Glu.Na was used (the pH value was 1.72); and ■-■ is a curve which shows the stability of josamycin attained when 300 mg of Glu.Na was used (the pH value was 2.14); and ●-● is a curve which shows the stability of josamycin attained when 400 mg of Glu.Na was used (the pH value was 2.66); and is a curve which shows the stability of josamycin attained when 500 mg of Glu.Na was used (the pH value was 3.14).

The results herein indicate that the stability of josamycin was very much enhanced by the use of Glu.Na.

EXAMPLE 11

Stabilization of 9-propionyljosamycin 200 mg of 9-propionyljosamycin was dissolved into 40 ml of Japan Pharmacopoeia 1st solution (pH 1.2) cooled in an ice bath. On the occasion, 150–900 mg glycine was added thereto as stabilizer (no glycine was used for the control). Then, after this solution was placed in a vessel whose temperature is kept constant in a thermostat at 37° C., sampling of 3 ml thereof was conducted in a lapse of time (after 15 minutes, 30 minutes and 60 minutes). Then, pH of this solution was adjusted to be at 9–10 by adding 4 ml of 10% w/w aqueous solution of sodium carbonate to each solution and it was extracted three times with 10 ml of ethyl acetate each. The extracted solution was concentrated under reduced pressure and the residue was dissolved into 1 ml of chloroform. Then, 2 μl of the solution (about 30 μg in terms of weight) was charged onto a silicagel thin layer plate (Merck art. 5715) and was developed by using the developing solvents comprising chloroform, methanol, acetic acid and water at the ratio of 79:7:7:1 and benzene, ethyl acetate and methanol at the ratio of 11:4:1, respectively, and the relative ratio of the spot of 9-propionyljosamycin and those of the decomposites thereof was measured by a densitometer (wavelength of 232 nm was used).

Figure 11:
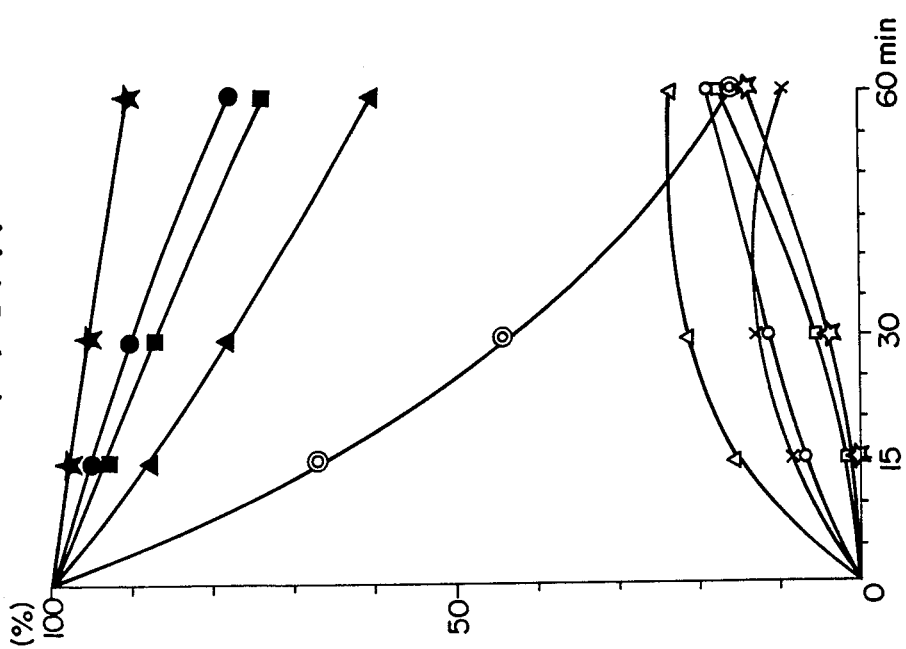
FIG. 11 shows the change in stability of propionyl-josamycin in a lapse of time, the change in formation ratio of the components in a lapse of time which is formed as the result of decomposition of 9-propionyl josamycin, and a curve of stabilization of 9-propionyl josamycin attained by the addition of glycin.

The results are as indicated in FIG. 11, wherein ⊚-⊚ indicates a curve of the changes in stability of 9-propionyljosamycin in a lapse of time as the control (in which no glycine was used); Δ-Δ indicates the formation ratio of josamycin which was generated as the result of decomposition thereof during change in a lapse of time; X—X indicates the formation ratio of 9-propionyl-demycarosyljosamycin which was generated as a lapse of time; ○-○ indicates a curve of the formation ratio of 9-deoxy-10,12-dedieno-9, 11-dien-13-hydroxy-josamycin (iso-josamycin); ◻-◻ indicates a curve of the formation ratio of demycarosyl josamycin which was generated as the result of change in a lapse of time; and ☆-☆ indicates a curve of the formation ratio of 9-deoxy-10,12-dedieno-9,11-dien-13-hydroxy-demycarosyl-josamycin (iso-demycarosiljosamycin).

As shown in FIG. 11, 9-propionyljosamycin is extremely unstable in the 1st solution which indicates a pH value equivalent to that of gastric juice. For example, the residual amount of 9-propionyljosamycin after the contact for 30 minutes with the 1st solution became only 44.2%, and the balance of 55.8% was decomposites thereof, and after the contact for 60 minutes, the residual amount of 9-propionyljosamycin was only 15.9% and the balance of 84.1% became decomposites thereof. When the similar procedures was followed by using 9propionyljosamycin syrup which was sold in the market, the results obtained were almost identical to those shown in FIG. 11.

On the contrary, in case glycine was used, which is indicated as a stabilizer in the present invention, 9-propionyljosamycin was stabilized well; in FIG. 11, ▲-▲ is a curve indicating the stability of 9-propionyljosamycin attained when 150 mg of glycine was used (at the time, the pH value was 1.71), ■-■ is a curve indicating the stability of 9propionyljosamycin attained when 300 mg of glycine was used (the pH value was 2.27); and ●-● is a curve which shows the stability of 9-propionyjosamycin when 400 mg of glycine was used (the pH value was 2.49); and further ★-★ is a curve which indicates the stability of 9-propionyljosamycin when 900 mg of glycine was used (pH value was 2.98). Under the present invention, the stability attained when 150 mg of glycine was used (▲-▲) improved by four times compared with the control (in terms of the value at 60 minutes), and by the use of a larger amount of glycine, stability of 9-propionyljosamycin was achieved to such a level that it was hardly decomposed.

EXAMPLE 12

In place of glycine in Example 11 above, 150–300 mg of calcium phosphate was used hereunder to test stability of 9-propionyljosamycin in the same procedures as those applied in Example 11.

Figure 12:
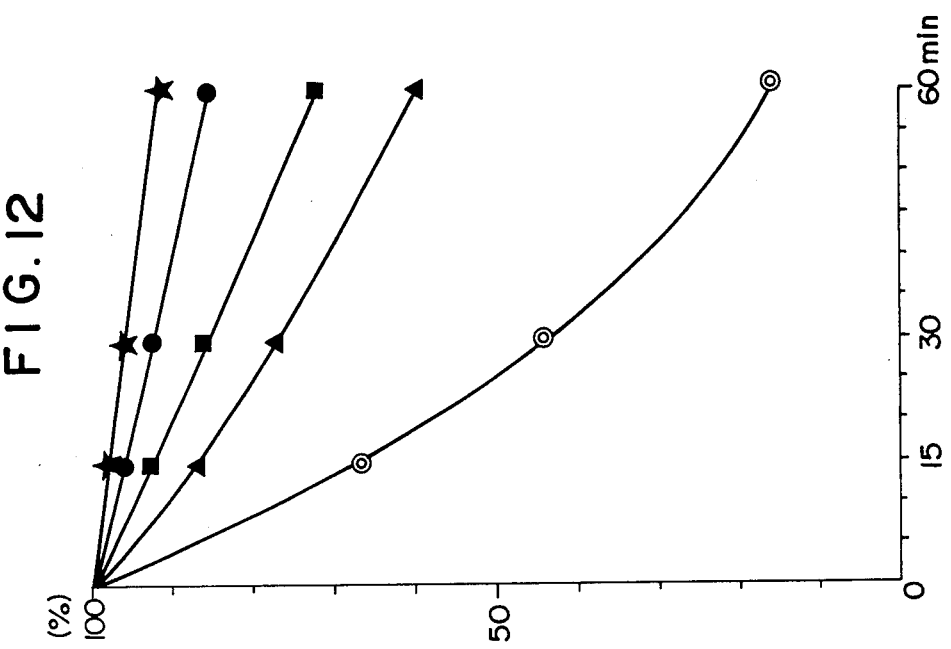
FIG. 12 shows a curve of stabilization of 9-propionyl josamycin attained by the addition of calcium phosphate.

The results of such test are as shown in FIG. 12, wherein ⊚-⊚ indicates a curve of the changes in stability of 9-propionyljosamycin in a lapse of time as the control (in the case no calcium phosphate was used). In FIG. 12, ▲-▲ indicates a curve which shows the stability of 9-propionyljosamycin attained when 150 mg of calcium phosphate was used (the pH value was 1.73); and ■-■ is a curve which shows the stability of 9-propionyljosamycin attained when 250 mg of calcium phosphate was used (the pH value was 2.22); and ●-● is a curve which shows the stability of 9-propionyljosamycin attained when 300 mg of calcium phosphate was used (the pH value was 2.71); and ★ - ★ represents a curve which shows the stability of 9-propionyljosamycin attained when 400 mg of calcium phosphate was used (the pH value was 3.16).

The results obtained herein indicate that the stability of 9-propionyljosamycin was extremely enhanced by the use of calcium phosphate.

EXAMPLE 13

In place of glycine in Example 11, 150–300 mg of tri-sodium citrate was used hereunder to test stability of 9-propionyljosamycin in the same procedures as those applied in Example 11.

Figure 13:
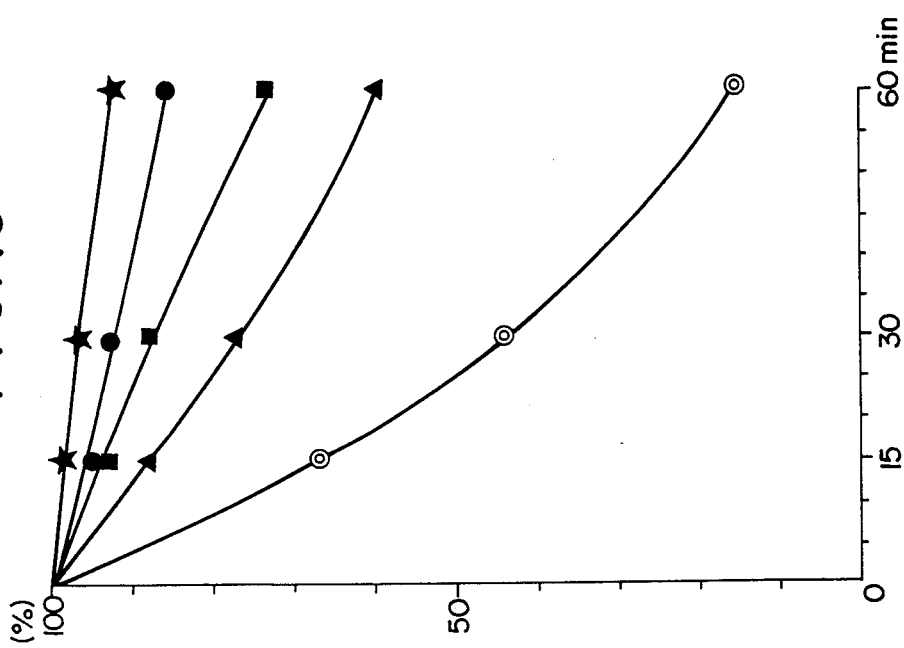
FIG. 13 shows a curve of stabilization of 9-propionyl josamycin attained by the addition of trisodium citrate.

The results of such test are as shown in FIG. 13, wherein ⊚ - ⊚ indicates a curve of the changes in stability of 9-propionyljosamycin in a lapse of time as the control (in the case no tri-sodium citrate was used). In FIG. 13, ▲ - ▲ indicates a curve which shows the stability of 9-propionyljosamycin attained when 150 mg of tri-sodium citrate was used (the pH value was 1.69); and ■ - ■ is a curve which shows the stability of 9-propionyljosamycin attained when 225 mg of tri-sodium citrate was used (the pH value was 2.34); and ● - ● is a curve which shows the stability of 9-propionyljosamycin attained when 250 mg of tri-sodium citrate was used (the pH value was 2.72); and is a curve which shows the stability of 9-propionyljosamycin attained when 300 mg of tri-sodium citrate was used (the pH value was 3.32).

The results herein indicate that the stability of 9-propionyljosamycin was very much enhanced by the use of tri-sodium citrate.

EXAMPLE 14

In place of glycine in Example 11 above, 200–500 mg of Asp.Na was used hereunder to test stability of 9-propionyljosamycin in the same procedures as those applied in Example 11.

Figure 14:
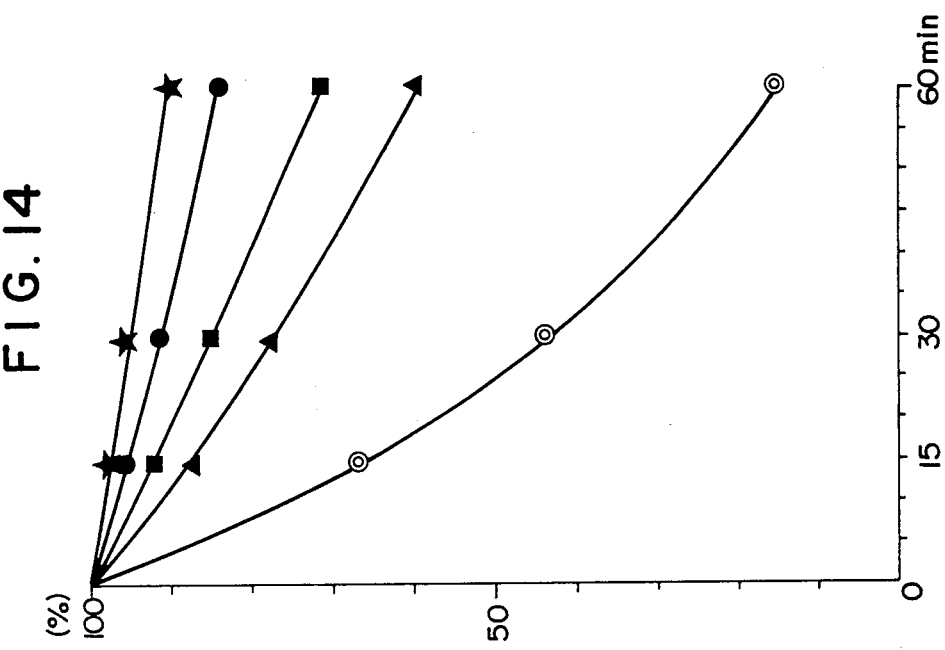
FIG. 14 shows a curve of stabilization of 9-propionyl josamycin attained by the addition of monosodium L-asparaginate.

The results of such test are as shown in FIG. 14, wherein ⊚ - ⊚ indicates a curve of the changes in stability of 9-propionyljosamycin in a lapse of time as the control (in the case no Asp.Na was used). In FIG. 14, ▲ - ▲ indicates a curve which shows the stability of 9-propionyljosamycin attained when 200 mg of Asp.Na was used (the pH value was 1.72); and ■ - ■ is a curve which shows the stability of 9-propionyljosamycin attained when 300 mg of Asp.Na was used (the pH value was 2.15); and ● - ● is a curve which shows the stability of 9-propionyljosamycin attained when 400 mg of Asp.Na was used (the pH value was 2.60); and ★ - ★ represents a curve which shows the stability of 9-propionyljosamycin when 500 mg of Asp.Na was used (the pH value was 3.04).

The results obtained herein indicate that 9-propionyljosamycin was very much enhanced by the use of Asp.Na.

EXAMPLE 15

In place of glycine in Example 11, 200–500 mg of Glu.Na was used hereunder to test stability of 9propionyljosamycin in the same procedures as those applied in Example 11.

Figure 15:
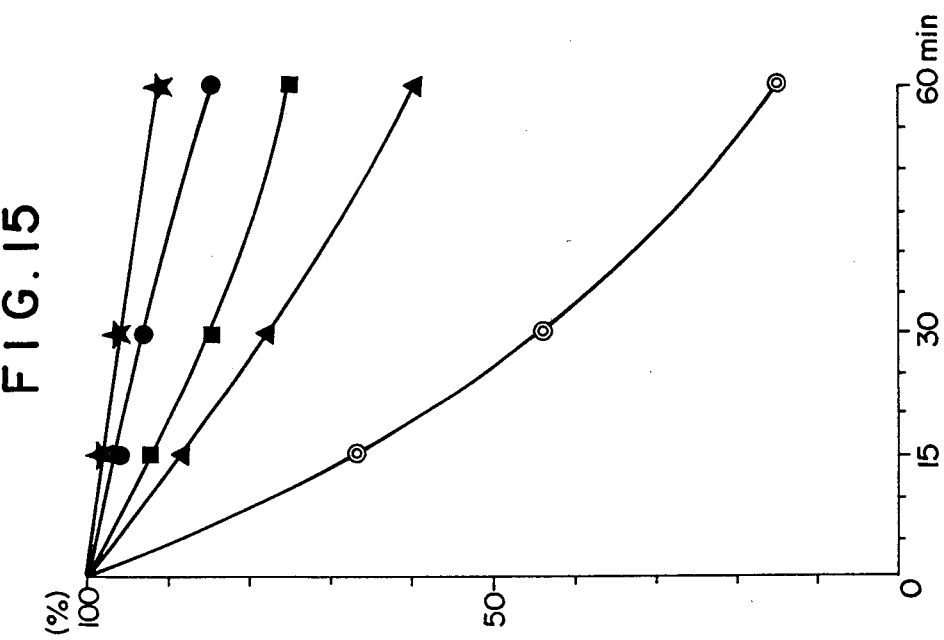
FIG. 15 shows a curve of stabilization of 9-propionyl josamycin attained by the addition of monosodium L-glutamate.

The results of such test are as shown in FIG. 15, wherein ⊚ - ⊚ indicates a curve of the changes in stability of 9-propionyljosamycin in a lapse of time as the control (in the case no Glu.Na was used). In FIG. 15, ▲ - ▲ indicates a curve which shows the stability of 9-propionyljosamycin attained when 200 mg of Glu.Na was used (the pH value was 1.70); and ■ - ■ is a curve which shows the stability of 9-propionyljosamycin attained when 300 mg of Glu.Na was used (the pH value was 2.16); and ● - ● a curve which shows the stability of 9-propionyljosamycin attained when 400 mg of Glu.Na was used (the pH value was 2.66); and ★ - ★ is a curve which shows the stability of 9-propionyljosamycin attained when 500 mg of Glu.Na was used (the pH value was 3.13).

The results obtained herein indicate that the stability of 9-propionyljosamycin was very much enhanced by the use of Glu.Na.

EXAMPLE 16

Stabilization of 3''-propionyl leucomycin $A_5$ 200 mg of 3''-propionyl leucomycin $A_5$ (hereinafter called "TMS-19-Q") was dissolved into 40 ml of Japan Pharmacopoeia 1st solution (pH 1.2) cooled in an ice bath. On the occasion, 150–900 mg glycine was added thereto as stabilizer (no glycine was used for the control). Then, after this solution was placed in a vessel whose temperature is kept constant in a thermostat at 37° C., sampling of 3 ml thereof was conducted in a lapse of time (after 15 minutes, 30 minutes and 60 minutes). Then, pH of this solution was adjusted to be at 9–10 by adding to each solution 4 ml of 10% w/w aqueous solution of sodium carbonate and it was extracted three times with 10 ml of ethyl acetate each. The extracted solution was concentrated under reduced pressure and the residue was dissolved into 1 ml of chloroform. Then, 2 μl of the solution (about 30 μg in terms of weight) was charged into a silicagel thin layer plate (Merck art. 5715) and was developed by using the developing solvent comprising chloroform, methanol, acetic acid and water at the ratio of 79:7:7:1 and the relative ratio of the spot of TMS-19-Q and those of the decomposites thereof were measured by a densitometer (wavelength of 232 nm was used).

Figure 16:
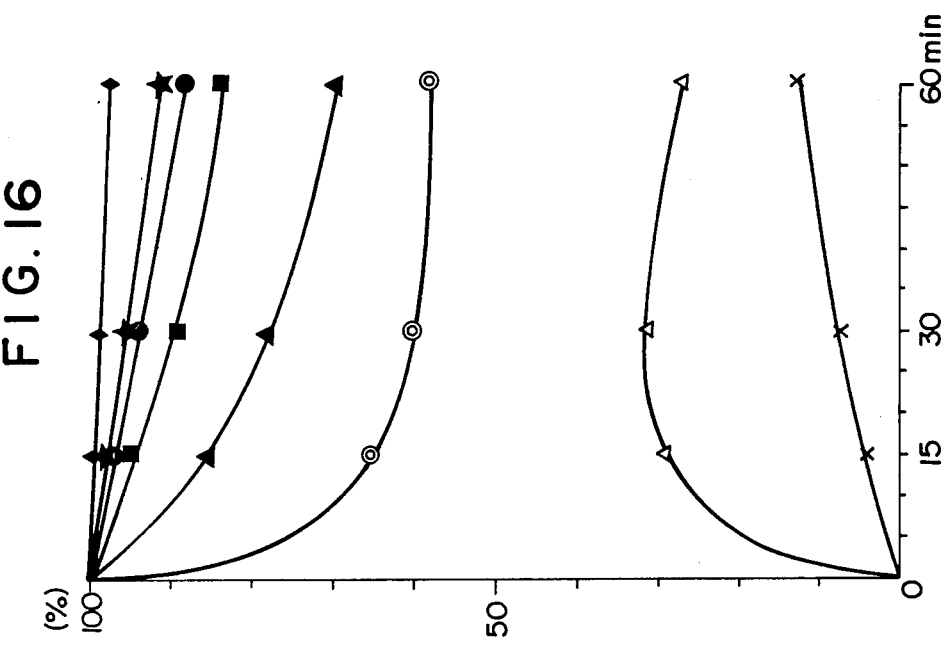
FIG. 16 shows the change in stability of TMS-19-Q in a lapse of time, change in formation ratio of the components formed as the result of decomposition of TMS-19-Q, and a curve of stabilization of TMS-19-Q attained by the addition of glycine.

The results are as indicated in FIG. 16, wherein ⊚ - ⊚ indicates a curve of the changes in stability of TMS-19-Q in a lapse of time as the control (in which no glycine was used) Δ - Δ indicates the formation ratio of 9-deoxy-10,12-dedieno-9,11-dien-13-hydroxy-TMS-19-Q and X - X indicates the formation ratio of 9-deoxy-10,12-dedieno-9,11-dien-13-epihydroxy-TMS-19-Q in a lapse of time. As shown in FIG. 16, TMS-19-Q is extremely unstable in the 1st solution which indicates a pH value equivalent to that of gastric juice. For example, the residual amount of TMS-19-Q after the contact for 30 minutes with 1st solution became only 60.5%, and the balance of 39.5% was decomposites thereof, and after the contact for 60 minutes, the residual amount of TMS-19-Q is 58.6% and the balance of 41.4% became decomposites thereof.

On the contrary, in case glycine was used, which is indicated as a stabilizer in the present invention, TMS-19-Q was stabilized well; in FIG. 16, ▲ - ▲ is a curve indicating the stability of TMS-19-Q attained when 150 mg of glycine was used (at the time, the pH value was 1.68); ■ - ■ is a curve indicating the stability of TMS-19-Q attained when 300 mg of glycine was used (the pH value was 2.31); ● - ● is a curve which shows the stability of TMS-19-Q attained when 350 mg of glycine was used (the pH value was 2.39); ★ - ★ is a curve which indicates the stability of TMS-19-Q attained when 400 mg of glycine was used (pH value was 2.51); and ✦ - ✦ is a curve indicating the stability of TMS-19-Q when 900 mg of glycine was used (pH value was 2.99). Under the present invention, the stability attained when 150 mg of glycine was used ▲ - ▲ improved by 30% compared with the control (in terms of the value at 30 minutes), and by the use of a larger amount of glycine, stability of TMS-19-Q was achieved to such a level that it got hardly decomposed.

EXAMPLE 17

In place of glycine in Example 16 above, 150–400 mg of calcium phosphate was used hereunder to test stability of TMS-19-Q in the same procedures as those applied in Example 16.

The results of such test are as shown in FIG. 17, wherein ⊚ - ⊚ indicates a curve of the changes in stability of TMS-19-Q in a lapse of time as the control (in the case no calcium phosphate was used). In FIG. 17, ▲ - ▲ indicates a curve which shows the stability of TMS-19-Q attained when 150 mg of calcium phosphate was used (the pH value was 1.73); and ■ - ■ is a curve which shows the stability of TMS-19-Q attained when 250 mg of calcium phosphate was used (the pH value was 2.21); and ● - ● is a curve which shows the stability of TMS-19-Q attained when 300 mg of calcium phosphate was used (the pH value was 2.70); and ★ - ★ represents a curve which shows the stability TMS- attained when 400 mg of calcium phosphate was used (the pH value was 3.16).

The results herein above indicate that the stability of TMS-19-Q was very much enhanced by the use of calcium phosphate.

EXAMPLE 18

In place of glycine in Example 16, 150–300 mg of tri-sodium citrate was used hereunder to test stability of TMS-19-Q in the same procedures as those applied in Example 16.

The results of such test are as shown in FIG. 18, wherein ⊚ - ⊚ indicates a curve of the changes in stability of TMS-19-Q in a lapse of time as the control (in the case no tri-sodium citrate was used). In FIG. 18, ▲ - ▲ indicates a curve which shows the stability of TMS-19-Q attained when 150 mg of tri-sodium citrate was used (the pH value was 1.67); and ■ - ■ is a curve which shows the stability of TMS-19-Q attained when 225 mg of tri-sodium citrate was used (the pH value was 2.34); and ● - ● is a curve which shows the stability of TMS-19-Q attained when 250 mg of tri-sodium citrate was used (the pH value was 2.72); and ★ - ★ is a curve which shows the stability of TMS-19-Q attained when 300 mg of tri-sodium citrate was used (the pH value was 3.32).

The results herein indicate that the stability of TMS-19-Q was very much enhanced by the use of trisodium citrate.

EXAMPLE 19

In place of glycine in Example 16 above, 200–500 mg of Asp.Na was used hereunder to test stability of TMS-19-Q in the same procedures as those applied in Example 16.

The results of such test are as shown in FIG. 19, wherein ⊚ - ⊚ indicates a curve of the changes in stability of TMS-19-Q in a lapse of time as the control (in the case no Asp.Na was used). In FIG. 19, ▲ - ▲ indicates a curve which shows the stability of TMS-19-Q attained when 200 mg of Asp.Na was used (the pH value was 1.72); and ■ - ■ is a curve which shows the stability of TMS-19-Q attained when 300 mg of Asp.Na was used (the pH value was 2.15); and ● - ● is a curve which shows the stability of TMS-19-Q attained when 400 mg of Asp.Na was used (the pH value was 2.60); and ★ - ★ represents a curve which shows the stability of TMS-19-Q attained when 500 mg of Asp.Na was used (the pH value was 3.04).

The results obtained herein indicate that the stability of TMS-19-Q was very much enhanced by the use of Asp.Na.

EXAMPLE 20

In place of glycine in Example 16, 200–500 mg of Glu.Na was used hereunder to test stability of TMS-19-Q in the same procedures as those applied in Example 16.

The results of such test are as shown in FIG. 20, wherein ⊚ - ⊚ indicates a curve of the changes in stability of TMS-19-Q in a lapse of time as the control (in the case no Glu.Na was used). In FIG. 20, ▲ - ▲ indicates a curve which shows the stability of TMS-19-Q attained when 200 mg of Glu.Na was used (the pH value was 1.70); and ■ - ■ is a curve which shows the stability of TMS-19-Q attained when 300 mg of Glu.Na was used (the pH value was 2.17); and ● - ● is a curve which shows the stability of TMS-19-Q attained when 400 mg of Glu.Na was used (the pH value was 2.66); and ★ - ★ is a curve which shows the stability of TMS-19-Q attained when 500 mg of Glu.Na was used (the pH value was 3.13).

The results herein indicate that the stability of TMS-19-Q was very much enhanced by the use of Glu.Na.

EXAMPLE 21

Stabilization of 9,3"-diacetylmidecamycin 200 mg of 9,3"-diacetylmidecamycin was dissolved into 40 ml of Japan Pharmacopoeia 1st solution (pH 1.2) cooled in an ice bath. On the occasion, 150–900 mg glycine was added thereto as stabilizer (no glycine was used for the control). Then, after this solution was placed in vessel whose temperature is kept constant in a thermostant at 37° C., sampling of 3 ml thereof was conducted in a lapse of time (after 15 minutes, 30 minutes and 60 minutes). Then pH of this solution was adjusted to be at 9–10 by adding 4 ml of 10% w/w aqueous solution of sodium carbonate to each solution and it was extracted three times with 10 ml of ethyl acetate each. The extracted solution was concentrated under reduced pressure and the residue was dissolved into 1 ml of chloroform. Then, 2 μl of the solution (about 30 μg in terms of weight) was charged into a silicagel thin layer plate (Merck art. 5715) and was developed by using the developing solvents comprising chloroform, methanol, acetic acid and water at the ratio of 79:7:7:1 and benzene, ethyl acetate and methanol at the ratio of 11:4:1, respectively, and the relative ratio of the spot of 9,3"-diacetylmidecamycin and those of the decomposites thereof were measured by a densitometer (wavelength of 232 nm was used).

The results are as indicated in FIG. 21, wherein ⊚ - ⊚ indicates a curve of the changes in stability of 9,3"-diacetylmidecamycin in a lapse of time as the control (in which no glycine was used); △ - △ indicates the formation ratio of 9-deacetyl-3"-acetylmidecamycin which was generated as the result of decomposition thereof during change in a lapse of time; X-X indicates the formation ratio of 9-deoxy-3"-acetyl10,12-dedieno-9,11-dien-13-hydroxymidecamycin which was generated as a lapse of time ○ - ○ indicates a curve of the formation ratio of an unknown substance which was produced by the decomposition in a lapse of time.

As shown in FIG. 21, 9,3″-diacetylmidecamycin is extremely unstable in the 1st solution which indicates a pH value equivalent to that of gastric juice. For example, the residual amount of 9,3″-diacetylmidecamycin after the contact for 30 minutes with the 1st solution became only 49.4% and the balance of 50.6% was decomposites thereof, and after the contact for 60 minutes, the residual amount of 9,3″-diacetylmidecamycin was only 24.5% and the balance of 75.5% became decomposites thereof.

On the contrary, in case glycine was used, which is indicated as a stabilizer in the present invention, 9,3″-diacetylmidecamycin was stabilized well; in FIG. 21, ▲ - ▲ is a curve indicating the stability of 9,3″-diacetylmidecamycin attained when 150 mg of glycine was used (at the time, the pH value was 1.70); ■ - ■ is a curve indicating the stability of 9,3″-diacetylmidecamycin attained when 300 mg of glycine was used (the pH value was 2.25); ● - ● is a curve which shows the stability of 9,3″-diacetylmidecamycin when 400 mg of glycine was used (the pH value was 2.50) and ★ - ★ is a curve which indicates the stability of 9,3″-diacetylmidecamycin when 900 mg of glycine was used (pH value was 2.96). Under the present invention, the stability attained when 150 mg of glycine was used (▲ - ▲) improved 60% compared with the control (in terms of the value at 30 minutes), and by the use of a larger amount of glycine, stability of 9,3″-diacetylmidecamycin was achieved to such a level that it got hardly decomposed.

EXAMPLE 22

In place of glycine in Example 21 above, 150–400 mg of calcium phosphate was used hereunder to test stability of 9,3″-diacetylmidecamycin in the same procedures as those applied in Example 21.

The results of such test are as shown in FIG. 22, wherein ◎ - ◎ indicates a curve of the changes in stability of 9,3″-diacetylmidecamycin in a lapse of time as the control (in the case no calciumphosphate was used). In FIG. 22, ▲ - ▲ indicates a curve which shows the stability of 9,3″-diacetylmidecamycin attained when 150 mg of calcium phosphate was used (the pH value was 1.71); and ■ - ■ is a curve which shows the stability of 9,3″-diacetylmidecamycin attained when 250 mg of calcium phosphate was used (the pH value was 2.24); and ● - ● is a curve which shows the stability of 9,3″-diacetylmidecamycin attained when 300 mg of calcium phosphate was used (the pH value was 2.73); and ★ - ★ represents a curve which shows the stability of 9,3″-diacetylmidecamycin attained when 400 mg of calcium phosphate was used (the pH value was 3.18).

The results obtained herein indicate that the stability of 9,3″-diacetylmidecamycin was extremely enhanced by the use of calcium phosphate.

EXAMPLE 23

In place of glycine in Example 21, 150–300 mg of tri-sodium citrate was used hereunder to test stability of 9,3″-diacetylmidecamycin in the same procedures as those applied in Example 21.

The results of such test are as shown in FIG. 23, wherein ◎ - ◎ indicates a curve of the changes in stability of 9,3″-diacetylmidecamycin in a lapse of time as the control (in the case no tri-sodium citrate was used). In FIG. 23 ▲ - ▲ indicates a curve which shows the stability of 9,3″-diacetylmidecamycin attained when 150 mg of tri-sodium citrate was used (the pH value was 1.69); and ■ - ■ is a curve which shows the stability of 9,3″-diiacetylmidecamycin attained when 225 mg of tri-sodium citrate was used (the pH value was 2.35); and ● - ● is a curve which shows the stability of 9,3″diacetylmidecamycin attained when 250 mg of tri-sodium citrate was used (the pH value was 2.72); and ★ - ★ is a curve which shows the stability of 9,3″-diacetylmidecamycin attained when 300 mg of tri-sodium citrate was used (the pH value was 3.32).

The results herein indicate that the stability of 9,3″-diacetylmidecamycin was very much enhanced by the use of tri-sodium citrate.

EXAMPLE 24

In place of glycine in Example 21 above, 200–500 mg of Asp.Na was used hereunder to test stability of 9,3″-diacetylmidecamycin in the same procedures as those applied in Example 21.

The results of such test are as shown in FIG. 24, indicates a curve of the changes in stability of 9,3″-diacetylmidecamycin in a lapse of time as the control (in the case no Asp.Na was used). In FIG. 24, ▲ - ▲ indicates a curve which shows the stability of 9,3″-diacetylmidecamycin attained when 200 mg of Asp.Na was used (the pH value was 1.73); and ■ - ■ is a curve which shows the stability of 9,3″-diacetylmidecamycin attained when 300 mg of Asp.Na was used (the pH value was 2.14); and ● - ● is a curve which shows the stability of 9,3″-diacetylmidecamycin attained when 400 mg of Asp.Na was used (the pH value was 2.62); and ★ - ★ is a curve which shows the stability of 9,3″-diacetylmidecamycin attained when 500 mg of Asp.Na was used (the pH value was 3.04).

The results obtained herein indicate that the stability of 9,3″-diacetylmidecamycin was very much enhanced by the use of Asp.Na.

EXAMPLE 25

In place of glycine in Example 21, 200–500 mg of Glu.Na was used hereunder to test stability of 9,3″diacetylmidecamycin in the same procedures as those applied in Example 21.

Figure 25:
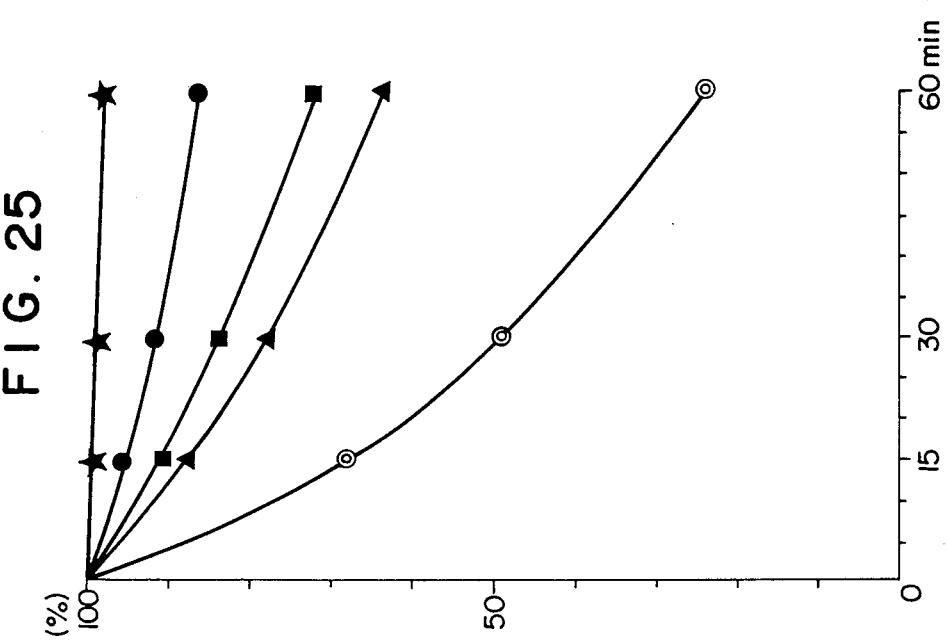
FIG. 25 shows a curve of stabilization of 9,3''-diacetyl midecamycin attained by the addition of monosodium L-glutamate.

The results of such test are as shown in FIG. 25, wherein ◎ - ◎ indicates a curve of the changes in stability of 9,3″-diacetylmidecamycin in a lapse of time as the control the case no Glu.Na was used). In FIG. 25, ▲ - ▲ a curve which shows the stability of 9,3″-diacetylmidecamycin attained when 200 mg. of Glu.Na was used (the pH value was 1.69); and ■ - ■ is a curve which shows the stability of 9,3″-diacetylmidecamycin attained when 300 mg of Glu.Na was used (the pH value was 2.15); ● - ● is a curve which shows the stability of 9,3″-diacetylmidecamycin attained when 400 mg of Glu.Na was used (the pH value was 2.68); and ★ - ★ represents a curve which shows the stability of 9,3″diacetylmidecamycin when 500 mg of Glu.Na was used (the pH value was 3.15).

The results obtained herein indicate that 9,3″-diacetylmidecamycin was very much enhanced by the use of Glu.Na.

EXAMPLE 26

After 40 ml of Japan Pharmacopoeia 1st solution (pH 1.2) was placed in a vessel whose temperature was kept constant in a thermostat at 37° C., 200 mg of TMS-19-Q was added and the mixture was stirred by a magnetic stirrer. Then, 5 ml samples thereof were taken in a lapse of time (at 15 minutes, 30 minutes and 60 minutes) to observe absorbance (wavelength: 232 nm) and elution rate was calculated. Then, Japan Pharmacopoeia 2nd solution were mixed with the 1st solution, and by using aqueous solutions whose pH values were adjusted to be 2, 3, 4 and 5 and a physiological saline solution, respectively, elution rate of each thereof was measured.

Figure 26:
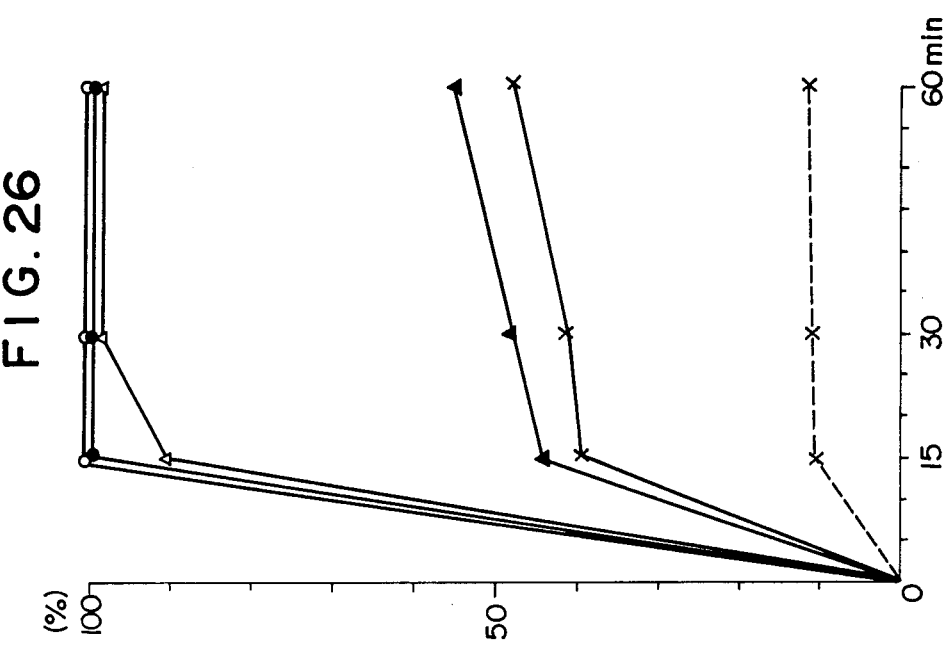
FIG. 26 shows a curve of elution of TMS-19-Q at various levels of pH.

The results are as indicated in FIG. 26. In FIG. 26, O-O, ●--●, Δ-Δ, ▲-▲, X—X X ... X indicate elution curves of aqueous solutions whose pH value are 1.2, 2, 3, 4 and 5 and of physiological saline solution, respectively. From the above, it was found that the elution rates of the aqueous solutions whose pH values were 1.2, 2 and 3, respectively, and whose samples were taken after 15-minute stirring were high, being equal to or more than 90%. However, in the case of the aqueous solutions whose pH value were 4 and 5, the elution rates thereof whose samples were taken after 15-minute stirring were at 40-45% and in the case of the physiological saline solution, the elution rate after 15-minute stirring was at an extremely low level of 10%. After a lapse of 60 minutes, the pH values of the aqueous solutions whose pH values were 1.2, 2, 3, 4 and 5 became 1.62, 2.51, 4.52, 5.90 and 5.85, respectively, and pH of the physiological saline solution became 5.87. In case of solutions whose pH is equal to or less than 4.5, the elution rates thereof were such that elution was nearly completed within 15 minutes.

EXAMPLE 27

To 40 ml of physiological saline solution 120 ml of water was added, and after the solution was placed in a vessel whose temperature was kept constant in a thermostat at 37° C., 200 mg of TMS-19-Q, 340 mg of glycine and 0-80 mg of citric acid were added, and the mixture was stirred by a magnetic stirrer. Then sampling thereof was conducted in a lapse of time (at 5 minutes, 15 minutes and 30 minutes) to observe absorbance (wavelength: 232 nm) and elution rate was calculated.

The results are as indicated in FIG. 27. In FIG. 27, O-O, ●-●, Δ-Δ, ▲-▲, X—X and X ... X indicate the elution curves of the solutions to which 80 mg, 60 mg, 40 mg, 20 mg, 10 mg and 0 mg of citric acid were added, respectively. From these curves of elution rates, it was found that the elution rates of the aqueous solutions to which citric acid in amounts equal to or more than 40 mg was added, respectively were excellent, being equal to or more than 95%. However, in the case of the aqueous solutions to which 20 mg or 10 mg of citric acid were added, the elution rates thereof taken after 15-minute stirring was 45-55%, and in the case of the aqueous solution to which 0 mg of citric acid was added, the elution rate after 15-minute stirring was at an extremely low level of 10%. After a lapse of 30 minutes, the pH values of the aqueous solutions of 80 mg, 60 mg, 40 mg, 20 mg, 10 mg, and 0 mg of citric acid became 3.84, 4.00, 4.23, 5.08, 5.40 and 5.87, respectively. In the case of solutions whose pH is equal to or less than 4.23, the elution rate thereof was such that elution was nearly completed within 15 minutes.

EXAMPLE 28

To 40 ml of physiological saline solution 120 ml of water was added, and after the solution was kept in a vessel whose temperature was kept constant in a thermostat controlled at 37° C., 200 mg of TMS-19-Q, 340 mg of glycine and 0-80 mg of tartaric acid were added, and the same procedures as those of Example 27 were followed to examine the elution rate of TMS-19-Q.

The results are as indicated in FIG. 28. In FIG. 28, O-O, ●-●, Δ-Δ, ▲-▲, X—X and X ... X indicate the elution curves of the solutions to which 80 mg, 60 mg, 40 mg, 20 mg, 10 mg and 0 mg of tartaric acid were added, respectively. From these curves of elution rates, it was found that the elution rates of the aqueous solutions to which tartaric acid in amounts equal to or more than 40 mg was added, respectively were excellent, being equal to or more than 95% in terms of the value at 15 minutes. However, in the case of the aqueous solutions to which 20 mg or 10 mg of tartaric acid were added, the elution rates thereof taken after 15-minute stirring was 40-55%, and in the case of the aqueous solution which 0 mg of tartaric acid was added, the elution rate after 15-minute stirring was at an extremely low level of 10%. After a lapse of 30 minutes, the pH values of the aqueous solutions of 80 mg, 60 mg, 40 mg, 20 mg, 10 mg, and 0 mg of tartaric acid became 3.77, 3.95, 4.09, 4.96, 5.32 and 5.87, respectively. In the case of solutions whose pH is equal to or less than 4.09, the elution rate thereof was such that elution was nearly completed within 15 minutes.

EXAMPLE 29

| [Granule A composition] | |
|---|---|
| TMS-19-Q | 105.3 g |
| Light anhydrous silicic acid | 30.0 g |
| HPMC (hydroxypropylmethyl cellulose, made by Shinetsu Chemical) | 7.0 g |
| [Granule B composition] | |
| Glycine | 170.0 g |
| Citric acid anhydride | 0-40 g |
| | (0 g, 10 g, 20 g 30 g, 40 g) |
| Light anhydrous silicic acid | 10.0 g |
| HPMC | 5.0 g |
| [Excipient etc.] | |
| L-HPC (low substituted-hydroxypropyl-cellulose, made by Shinetsu Chemical) | 40.0 g |
| Avicel PH 301 (made by Asahi Chemical) | 52.7–12.7 g (52.7 g, 42.7 g, 32.7 g, 22.7 g and 12.7 g) |
| Magnesium stearate | 10.0 g |
| Total | 430.0 g |

To a mixture comprising TMS-19-Q and light anhydrous silicic acid, 10% w/w HPMC aqueous solution was added. Then the mixture was kneaded, dried and sieved by the use of a 24 mesh sieve to obtain Granule A.

To a mixture comprising glycine, citric acid anhydride and light silicic acid, 5% w/w HPMC aqueous solution was added as binder, and the mixture was made into granules by fluidized bed method (FB method). Then the granules were dried and sieved through 24 mesh screen to obtain Granule B.

To Granule A and Granule B, L-HPC and Avicel PH301 (to be adjusted by an amount of citric acid added: 52.7–12.7 g) and magnesium stearate were added and mixed. Then, the mixed powder was molded by pressure to the size of 14×8 mm and tablets were obtained, each of which (430 mg) containing 100 mg potency of TMS-19-Q 170 mg glycine and citric acid (0, 10, 20, 30 and 40 mg).

Five tablets of 100 mg potency of TMS-19-Q containing citric acid at 0-40 mg, were orally administered to each of 8 beagle dogs (male; body weight: 10 kg) which had not been fed for 24 hours, together with 100 ml of water. Then, 2.5 cc blood was drawn therefrom in a lapse of time (at 15 minutes, 30 minutes, 1 hour, 2 hours, 4 hours and 6 hours) and the concentration of TMS-19-Q in the blood taken at each lapse of time was measured through the bioassay method (*Micrococcus luteus* ATCC 9341 test germ was used) and AUC at each level of citric acid was calculated.

Figure 29:
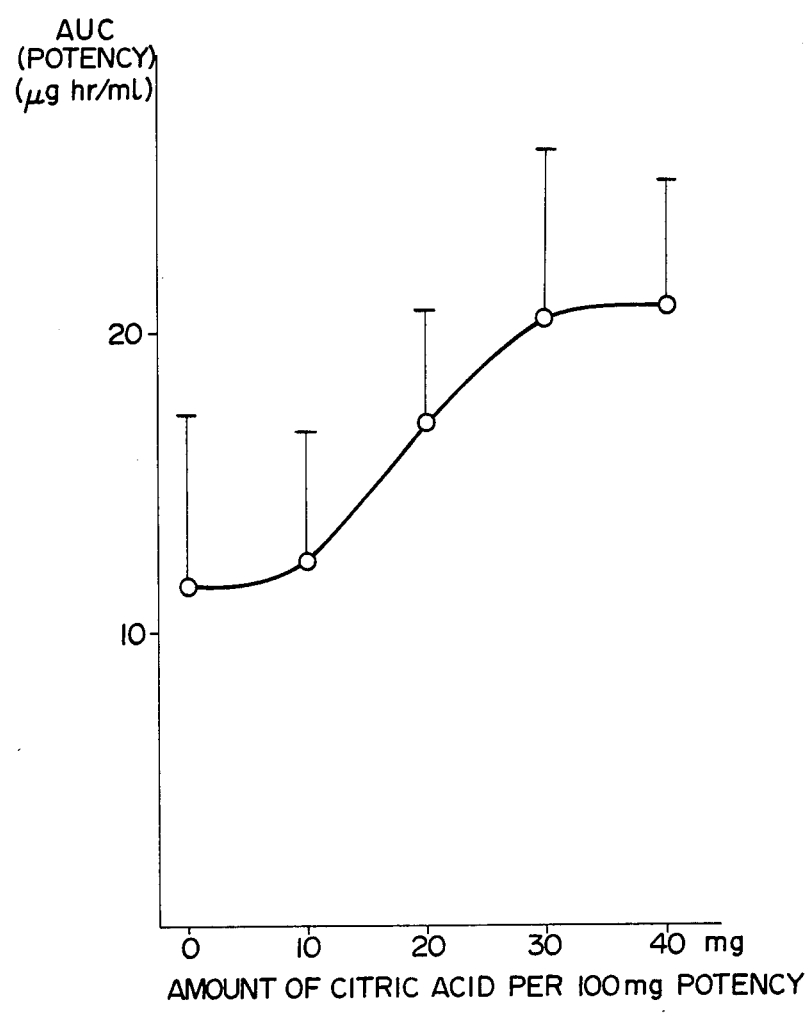
FIG. 29 shows the concentration of TMS-19-Q in the blood of beagles to which TMS-19-Q tablets were administered.

The results of average AUC are as shown in FIG. 29. It was found that AUC value reached saturation when the amount of citric acid was at 30-40 mg.

EXAMPLE 30

Figure 30:
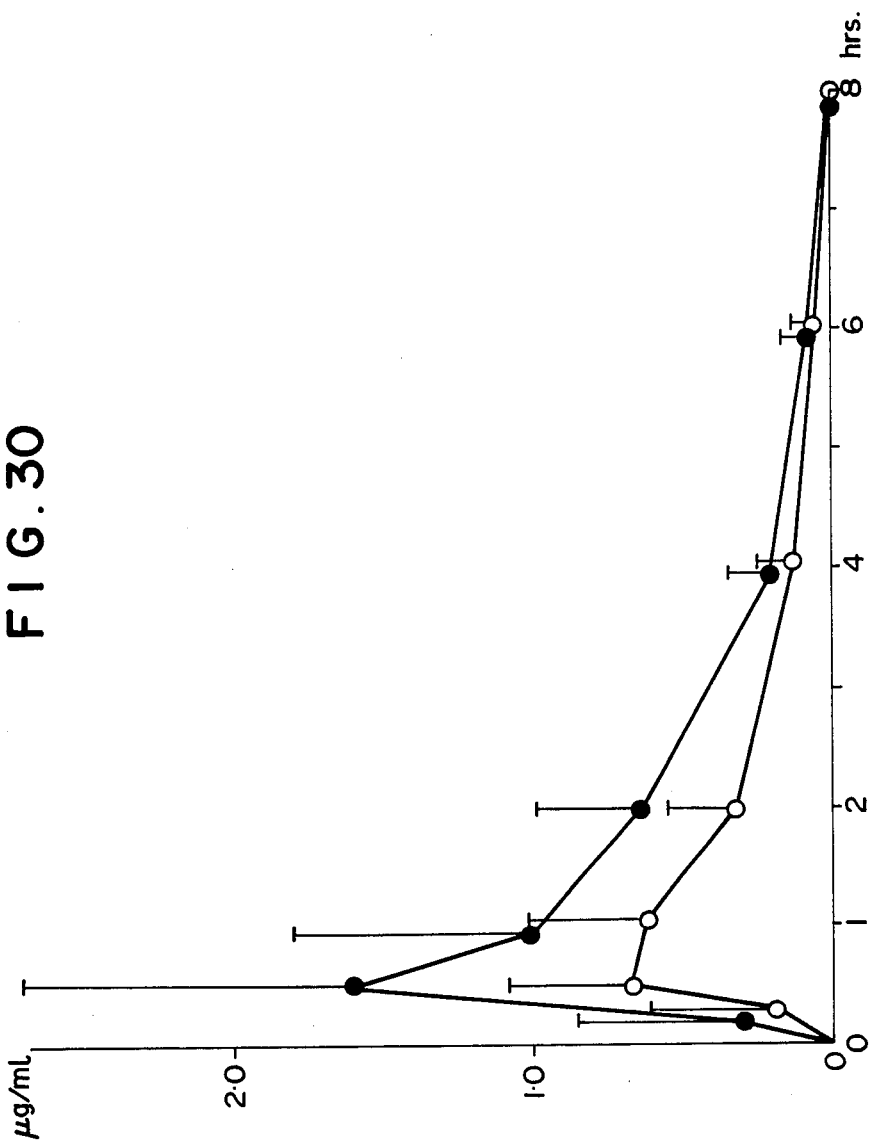
FIG. 30 shows the concentration of TMS-19-Q in the blood of patients to whom TMS-19-Q tablets were administered.
Figure 31:
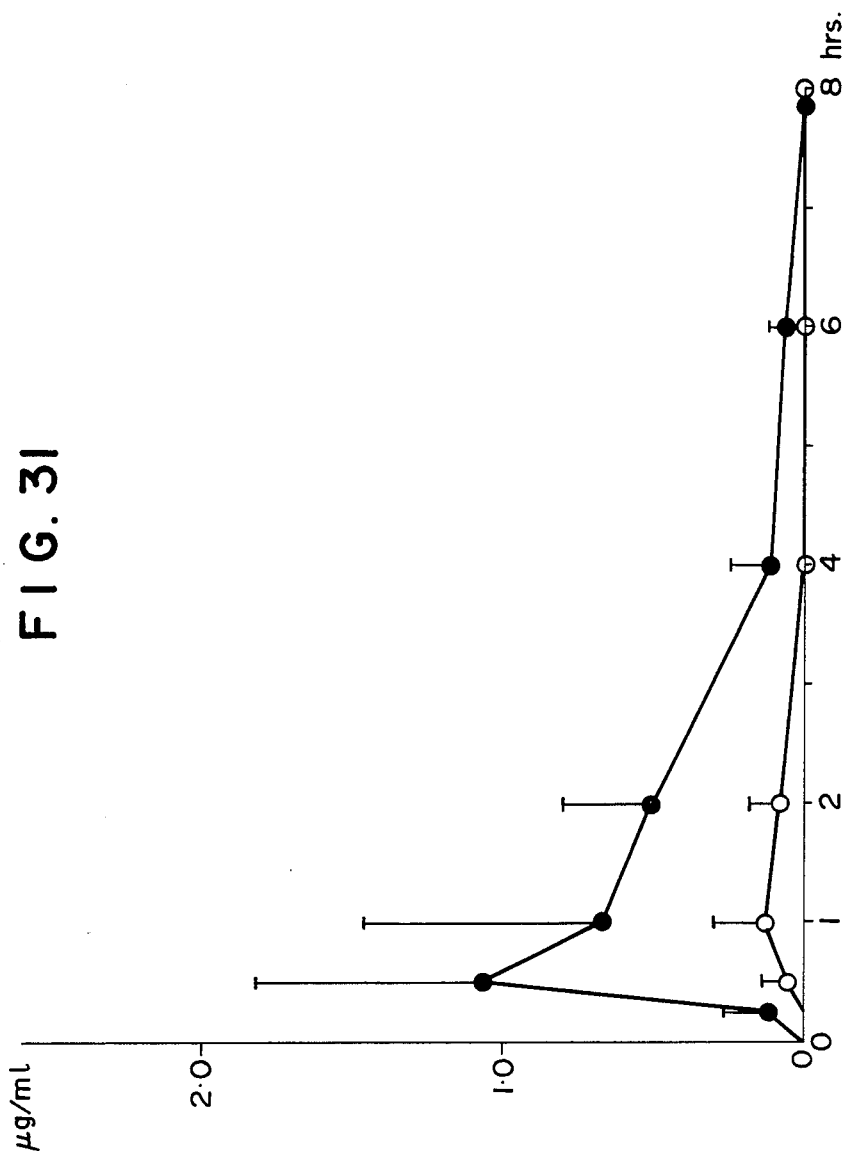
FIG. 31 shows the concentration of EMS-19-Q in the blood of the patients suffering from achlorhydria syndrome, to whom TMS-19-Q tablets were administered.

Six tablets of 100 mg potency of TMS-19-Q containing 170 mg of glycine and 35 mg of citric acid, which were prepared as described in Example 35 below, were administered to each of 14 healthy adults together with 120 ml of water when their stomachs were empty. Then, 5 ml blood was drawn therefrom in a lapse of time (at 15 minutes, 30 minutes, one hour, 2 hours, 4 hours, 6 hours and 8 hours), and the concentration of TMS-19-Q in the blood taken at each lapse of time was measured through the bioassay method. Furthermore, tablets of 100 mg potency TMS-19-Q out of which glycine and citric acid were removed by the use of the cross-over method were prepared following the procedures described in Example 35. After such tablets were administered in the same manner as described above, the concentrations of TMS-19-Q in the blood were measured. The average concentrations of TMS-19-Q in the blood of the 14 people were as shown in FIG. 30. In FIG. 30, ● - ● represents the average concentration in the blood of 100 mg potency of TMS-19-Q containing glycine and citric acid, and ○ - ○ represents the average concentration in the blood of 100 mg potency of TMS-19-Q containing neither glycine nor citric acid. From these curves of the concentration of TMS-19-Q in the blood, it was noted that in the case of TMS-19-Q tablets containing glycine and citric acid, AUC was 3.05 μg potency·hr/ml, while in the case of TMS-19-Q tablets containing neither glycine nor citric acid, AUC was 1.65 μg potency·hr/ml. Thus, AUC of the TMS-19-Q tablets containing glycine and citric acid was two times higher which represents an improvement. Furthermore, the average concentration of TMS-19-Q in the blood of 6 achlorhydria syndrome patients among 14 adults are as shown in FIG. 31, wherein ● - ● represents a curve of the concentration in the blood of TMS-19-Q in the tablets containing glycine and citric acid; and ○ - ○ represents a curve of the concentration in the blood of TMS-19-Q in the tablets containing neither glycine nor citric acid. From these curves of the TMS-19-Q concentration in the blood, it was noted that AUC of TMS-19-Q tablets containing glycine and citric acid was 1.99 μg potency·hr/ml, while AUC of TMS-19-Q tablets containing neither glycine nor citric acid was 0.23 μg potency·hr/ml. Thus, the TMS-19-Q tablets containing glycine and citric acid represented about 5 times improvement.

EXAMPLE 31

To 40 ml of Japan Pharmacopoeia 1st solution (pH 1.2), 120 ml of water was added, and after the solution was kept in a constant temperature bath controlled at 37° C., 200 mg of midecamycin was added, and the mixture was stirred by a magnetic stirrer. Then, 5 ml aliquots of the solution were sampled in a lapse of time (at 5 minutes, 15 minutes and 30 minutes), and absorbances were measured (wavelength: 232 nm) and elution rate were calculated. Then, Japan Pharmacopoeia 1st solution and Japan Pharmacopoeia 2nd solution were mixed to prepare aqueous solutions whose pH values were adjusted to be 2, 3, 4 and 5, respectively. By using these solutions and physiological saline solution, the elution rates were calculated following the same procedures as those indicated above.

Figure 32:
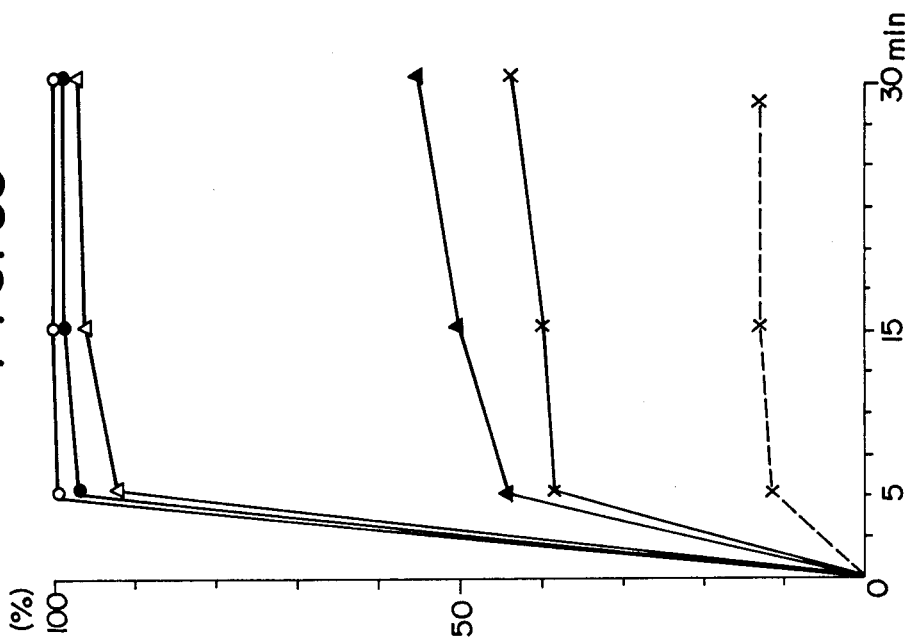
FIG. 32 shows a curve of eolution of midecamycin against pH.

The results are as indicated in 32. In FIG. 32, - , ○ -○ , △ -△ , ▲ -▲ , X—X and X . . . X, indicate the elution curves of the aqueous solutions having pH at 1.2, 2, 3, 4 and 5 and of the physiological saline solution, respectively. From these curves of elution rates, it was found that the elution rates of the samples of the aqueous solutions with pH at 1.2, 2 and 3 which were taken after 15-minute stirring were excellent, being equal to or more than 95%. However, in the case of the aqueous solutions with pH at 4 and 5 the elution rates thereof taken after 15-minute stirring was 45-60%, and in the case of the physiological saline solution the elution rate after 15-minute stirring was at an extremely low level of 15%. After a lapse of 30 minutes, the pH values of the aqueous solutions with pH at 1.2, 2, 3, 4 and 5 and of the physiological saline solution became 1.68, 2.94, 4.37, 5.66, 5.74 and 5.85, respectively. In the case of solutions whose pH is equal to or less than 4.37, the elution rate thereof was such that elution was nearly completed within 15 minutes.

EXAMPLE 32

By following the same procedures and under the same conditions as those of Example 31, elution rates of 9-propionyljosamycin were measured.

Figure 33:
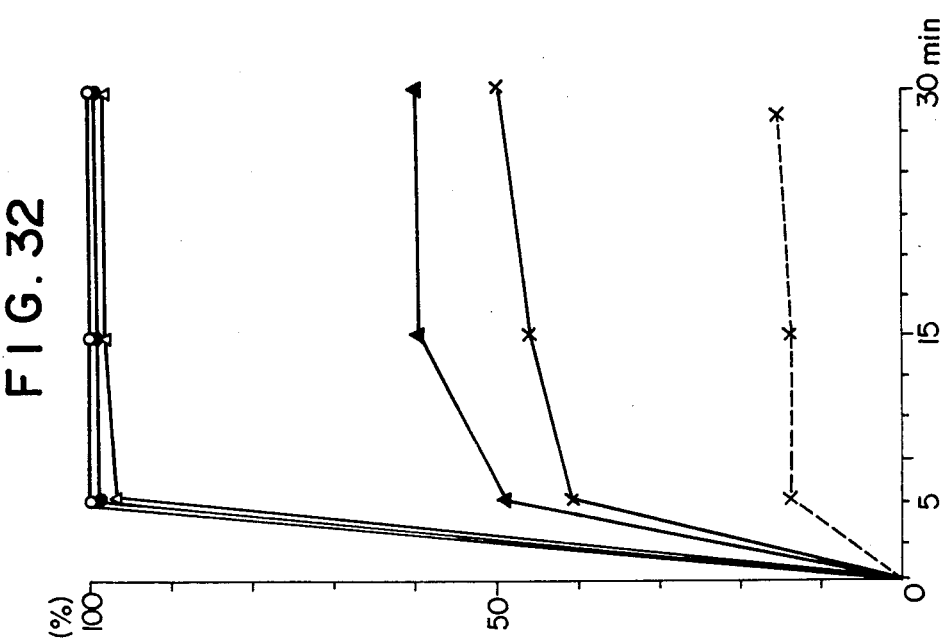
FIG. 33 shows a curve of elution of 9-propionyl josamycin against pH.

The results are as indicated in FIG. 33. In FIG. 33, ○ — ○ , ● — ● , △ — △ , ▲ — ▲ , X—X and X . . . X, indicate the elution curves of the aqueous solutions having pH of 1.2, 2, 3, 4 and 5 and of the physiological saline solution, respectively. From these curves of elution rates, it was found that the elution rates of the samples of the aqueous solutions having pH of 1.2, 2 and 3 which were taken after 15-minute stirring were excellent, being equal to or more than 95%. However, in the case of the aqueous solutions having pH of 4 and 5, the elution rates thereof taken after 15-minute stirring was 45-55%, and in the case of the physiological saline solution the elution rate after 15-minute stirring was at an extremely low level of 10%. After a lapse of 30 minutes, the pH values of the aqueous solutions having pH of 1.2, 2, 3, 4 and 5 and of the physiological saline solution became 1.69, 2.98, 4.37, 5.67, 5.76 and 5.84, respectively. In the case of solutions whose pH is equal to or less than 4.37, the elution rate thereof was such that elution was nearly completed within 15 minutes.

EXAMPLE 33

By following the same procedures and under the same conditions as those of Example 31, elution rates of josamycin were measured.

Figure 34:
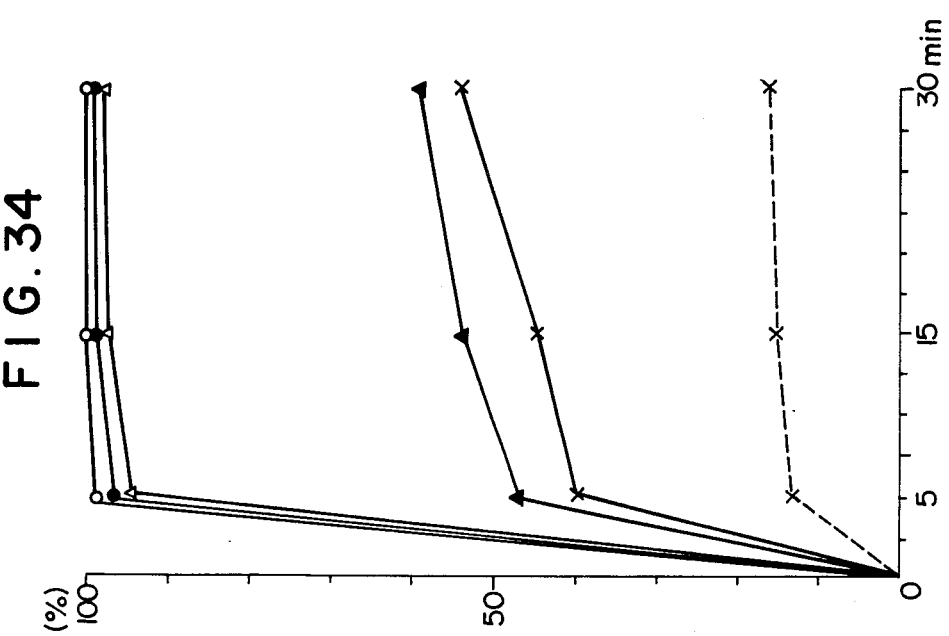
FIG. 34 shows a curve of elution of josamycin against pH.

The results are as indicated indicated in FIG. 34. In FIG. 34, ○ — ○ , ● — ● , △ — △ , ▲ — ▲ , X—X and X . . . X indicate the elution curves of the aqueous solutions having pH of 1.2, 2, 3, 4 and 5 and of the physiological saline solution, respectively. From these curves of elution rates, it was found that the elution rates of the samples of the aqueous solutions having pH of 1.2, 2 and 3 which were taken after 15-minute stirring were excellent, being equal to or more than 95%. However, in the case of the aqueous solutions having pH of 4 and 5 the elution rates thereof taken after 15-minute stirring was 50–60%, and in the case of the physiological saline solution, the elution rate after 15-minute stirring was at an extremely low level of 15%. After a lapse of 30 minutes, the pH values of the aqueous solutions having pH of 1.2, 2, 3, 4 and 5 and of the physiological saline solution became 1.65, 2.95, 4.35, 5.65, 5.72 and 5.82, respectively. In the case of solutions whose pH is equal to or less than 4.35, the elution rate thereof was such that elution was nearly completed within 15 minutes.

EXAMPLE 34

In addition to the conditions of Example 31, Japan Pharmacopoeia 1st solution and Japan Parmacopoeia 2nd solution were mixed to prepare an aqueous solution having pH of 2.5, and following the same procedures as those of Example 31, elution rates of 9,3″-diacetyl-midecamycin were measured.

Figure 35:
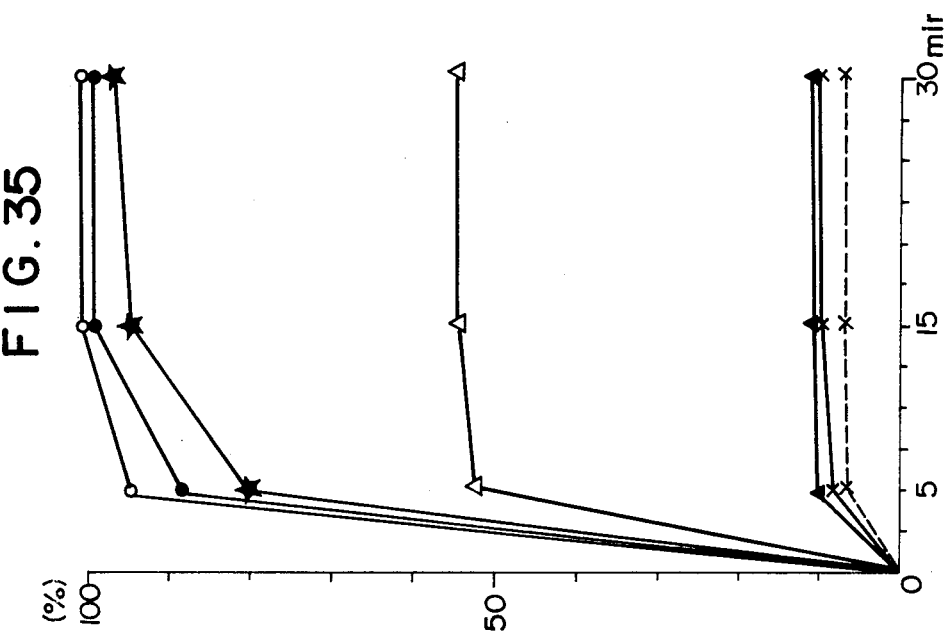
FIG. 35 shows a curve of elution of 9,3''-diacetyl midecamycin agains pH.

The results are as indicated in FIG. 35. In FIG. 35, ○ — ○ , ● — ● , ★ — ★ , △ — △ , ▲ — ▲ , X—X and X . . . X indicate the elution curves of the aqueous solutions with pH at 1.2, 2, 2.5, 3, 4 and 5 and of the physiological saline solution, respectively. From these curves of elution rates, it was found that the elution rates of the samples of the aqueous solutions having pH of 1.2, 2 and 2.5 which were taken after 15-minute stirring were excellent, being equal to or more than 95%. However, in the case of the aqueous solution with pH 3 the elution rates after 15-minute stirring was 50%. Those solutions with pH having 4 and 5 and the physiological saline solution gave the elution rates after 15-minute stirring were at an extremely low level of 5–10%. After a lapse of 30 minutes, the pH values of the aqueous solutions having pH of 1.2, 2.0, 2.5, 3, 4 and 5 and of the physiological saline solution became 1.96, 2.95, 3.77, 4.37, 5.63, 5.77 and 5.80, respectively. In the case of solutions whose final pH is equal to or less than 3.77, the elution rate thereof was such that elution was nearly completed within 15 minutes.

EXAMPLE 35

| [Granule A composition] | |
|---|---|
| TMS-19-Q | 105.3 g |
| Light anhydrous silicic acid | 30.0 g |
| HPMC | 7.0 g |
| [Granule B composition] | |
| Glycine | 170.0 g |
| Citric anhydride | 35.0 g |
| Light anhydrous silicic acid | 10.0 g |
| HPMC | 5.0 g |
| [Excipient etc.] | |
| L-HPC | 40.0 g |
| Avicel pH 301 | 17.7 g |
| Magnesium stearate | 10.0 g |
| Total | 430.0 g |

To a mixture comprising TMS-19-Q and light anhydrous silicic acid, 10% (w/w) HPMC aqueous solution was added. Then, the mixture was kneaded, dried and sieved by the use of a 24 mesh sieve to obtain Granule A.

To a mixture comprising glycine, citric acid anhydride and light anhydrous silicic acid, 5% (w/w) HPMC aqueous solution was added as spray binder, and the mixture was made into granules by FB method. Then, the granules were dried and sieved by the use of a 24 mesh sieve to obtain Granule B. To Granule A and Granule B, L-HPC, Avicel pH 301 and magnesium stearate were added and mixed. Then, the mixed powder was molded by pressure to the size of 14×8 mm and tablets were obtained, each (430 mg) of which containing 100 mg potency of TMS-19-Q, 170 mg of glycine and 35 mg of citric acid.

Two tablets thus obtained were used to measure elution rates in which 40 ml each of the aqueous solutions whose pHs were adjusted at 1.2, 2, 3, 4 and 5 and the physiological saline solution and 120 ml of water were used to obtain elution rate (hereinafter "elution rate by the stirrer method (200 rpm)" will be abridged to "elution rate"). The results were excellent, indicating that at each level of pH, the elution rates of the samples taken after 15-minute stirring were equal to or more than 95%.

EXAMPLE 36

| <Recipe> | |
|---|---|
| TMS-19-Q | 105.3 g |
| Glycine | 170.0 g |
| Citric acid anhydride | 35.0 g |
| Light anhydrous silicic acid | 30.0 g |
| Purified sucrose | 649.7 g |
| HPMC | 10.0 g |
| Total | 1,000.0 g |

To a mixture comprising TMS-19-Q, glycine, citric acid anhydride, light anhydrous silicic acid and purified sucrose, 10% (w/w) HPMC aqueous solution was added. Then the mixture was kneaded. This kneaded substance was made into granules by a cylinder-type granulator and they were dried to obtain granules, whose 1 g contains 100 mg potency of TMS-19-Q, 170 mg of glycine and 35 mg of citric acid. The results of the elution rate measurements by the use of 2 g of the granule agent were excellent, showing that at each level of pH, the elution rate after 15-minute stirring was equal to or more than 95%.

EXAMPLE 37

| <Recipe> | |
|---|---|
| TMS-19-Q | 105.3 g |
| Glycine | 170.0 g |
| Citric acid anhydride | 35.0 g |
| Purified sucrose | 669.7 g |
| HPMC | 20.0 g |
| Total | 1,000.0 g |

The mixture comprising TMS-19-Q, glycine, citric acid anhydride and purified sucrose was made into granules by FB method. 5% (w/w) HPMC (in 50% alcoholic solution) was used as a binder in preparing the granules. After drying, the granules were sieved by a 30 mesh sieve, and fine granules whose 1 g contains 100 mg potency of TMS-19-Q, 170 mg of glycine and 35 mg citric acid. The results of the elution rate measurements through the stirrer method in which 2 g of these fine granules were used were excellent, showing that at each level of pH, the elution rate after 15-minute stirring was equal to or more than 95%.

EXAMPLE 38

| [Granule A composition] | |
|---|---|
| TMS-19-Q | 105.3 g |
| Light anhydrous silicic acid | 30.0 g |
| HPMC | 7.0 g |
| [Granule B composition] | |
| Glu.Na | 150.0 g |
| Tartaric acid | 35.0 g |
| Light anhydrous silicic acid | 10.0 g |
| HPMC | 5.0 g |
| [Excipient etc.] | |
| L-HPC | 40.0 g |
| Avicel pH 301 | 17.7 g |
| Magnesium stearate | 10.0 g |
| Total | 410.0 g |

By applying the same procedures as those of Example 35, tablets were obtained. Each tablet (410 mg) contained 100 mg potency of TMS-19-Q, 150 mg of Glu.Na and 35 mg of tartaric acid. The elution rate measurements by the stirrer method in which 2 tablets were used gave excellent results, showing that at each level of pH, the elution rate after 15-minute stirring was equal to or more than 95%.

EXAMPLE 39

| <Recipe> | |
|---|---|
| TMS-19-Q | 10.5 g |
| Calcium phosphate | 15.0 g |
| Citric acid anhydride | 3.5 g |
| Light anhydrous silicic acid | 3.0 g |
| Purified sucrose | 67.0 g |
| HPMC | 1.0 g |
| Total | 100.0 g |

By applying the same procedures as those of Example 36, granules, which contain 100 mg potency of TMS-19-Q, 150 mg calcium phosphate, 35 mg of citric acid per 1 g thereof, were obtained. The elution rate measurements by the stirrer method in which 2 g of granules were used gave excellent results showing that at each level of pH, the elution rate after 15-minute stirring was equal to or more than 95%.

EXAMPLE 40

| <Recipe> | |
|---|---|
| TMS-19-Q | 10.5 g |
| Asp.Na | 15.0 g |
| Citric acid anhydride | 3.5 g |
| Purified sucrose | 69.0 g |
| HPMC | 2.0 g |
| Total | 100.0 g |

By applying the same procedures as those of Example 37, fine granules, which contain 100 mg potency of TMS-19-Q, 150 mg of Asp.Na, 35 mg of citric acid per 1 g thereof, were obtained. The elution rate measurements by the stirrer method in which 2 g of fine granules were used gave excellent results showing that at each level of pH, the elution rate after 15-minute stirring was equal to or more than 95%.

EXAMPLE 41

| <Recipe> | |
|---|---|
| Midecamycin | 10.0 g |
| Calcium phosphate | 7.5 g |
| Citric acid anhydride | 1.8 g |
| Light anhydrous silicic acid | 1.5 g |
| Purified sucrose | 28.7 g |
| HPMC (TC-5) | 0.5 g |
| Total | 50.0 g |

To a mixture comprising above mentioned amounts of midecamycin, glycine, citric acid anhydride, light anhydrous silicic acid and purified sucrose, 10% (w/w) HPMC aqueous solution was added. Then the mixture was kneaded. This kneaded substance was made into granules by a cylinder-type granulator and they were dried to obtain granules, whose 1 g contains 200 mg potency of midecamycin, 150 mg of calcium phosphate and 36 mg of citric acid. The results of the elution rate measurements by the use of 2 g of the granules were excellent, showing that at each level of pH, the elution rate after 15-minute stirring was equal to more more than 95%.

EXAMPLE 42

| <Recipe> | |
|---|---|
| 9-propionyl-josamycin | 10.0 g |
| Glycine | 8.5 g |
| Citric acid anhydride | 1.8 g |
| Light anhydrous silicic acid | 1.5 g |
| Purified sucrose | 27.7 g |
| HPMC (TC-5) | 0.5 g |
| Total | 50.0 g |

By applying the same procedures as those of Example 36, granules, which contain per 1 g thereof 200 mg of 9-propionyl-josamycin, 170 mg of glycine, 36 mg of citric acid, were obtained. The elution rate measurements by the stirrer method, in which 2 g of granules were used, gave excellent results, showing that at each level of pH, the elution rate after 15-minute stirring was equal to or more than 95%.

EXAMPLE 43

| <Recipe> | |
|---|---|
| Josamycin | 10.0 g |
| Glycine | 8.5 g |
| Citric acid anhydride | 1.8 g |
| Light anhydrous silicic acid | 1.5 g |
| Purified sucrose | 27.7 g |
| HPMC (TC-5) | 0.5 g |
| Total | 50.0 g |

By applying the same procedures as those of Example 36, granules, which contain in 1 g thereof 200 mg of josamycin, 170 mg of glycine, 36 mg of citric acid were obtained. The elution rate measurements by the stirrer method, in which 2 g of granules were used, gave excellent results, showing that at each level of pH, the elution rate after 15-minute stirring was equal to or more than 95%.

EXAMPLE 44

| <Recipe> | |
|---|---|
| 9,3''-diacetyl-midecamycin | 5.0 g |
| Glycine | 8.5 g |
| Tartaric acid | 2.0 g |
| Light anhydrous silicic acid | 1.5 g |
| Purified sucrose | 32.5 g |
| HPMC (TC-5) | 0.5 g |
| Total | 50.0 g |

By applying the same procedures as those of Example 36, granules which contain per 1 g thereof 100 mg of 9,3''-diacetyl-midecamycin 170 mg of glycine, 40 mg of tartaric acid were obtained. The elution rate measurements by the stirrer method, in which 2 g of granules were used, gave excellent results, showing that at each level of pH, the elution rate after 15-minute stirring was equal to or more than 95%.

EXAMPLE 45

| [Granule A composition] | |
|---|---|
| TMS-19-Q | 105.3 g |
| Glycine | 70.0 g |
| Light anhydrous silicic acid | 20.0 g |
| HPMC | 10.0 g |
| [Granule B composition] | |
| Glycine | 100.0 g |
| Citric acid anhydride | 35.0 g |
| Light anhydrous silicic acid | 10.0 g |
| HPMC | 5.0 g |
| [Excipient etc.] | |
| L-HPC | 30.0 g |
| Avicel pH 301 | 6.7 g |
| Magnesium stearate | 8.0 g |
| Total | 400.0 g |

To a mixture comprising TMS-19-Q, glycine and light anhydrous silicic acid, 10% (w/w) HPMC aqueous solution was added. Then, the mixture was kneaded, dried and sieved by the use of a 32 mesh sieve to obtain Granule A.

To a mixture comprising glycine, citric acid anhydride and light anhydrous silicic acid, 10% (w/w) HPMC aqueous solution was added, and the mixture was kneaded. Then, the mixture were dried and sieved by the use of a 32 mesh sieve to obtain Granule B.

To granule A and Granule B, L-HPC, Avicel pH 301 and magnesium stearate were added and mixed. Then, the mixed powder was charged into capsules by Zanashi-LZ-64 (fabricated by Zanashi), each of which (400 mg) contains 100 mg potency of TMS-19-Q, 170 mg of glycine and 35 mg of citric acid.

The elution rates of the two capsules measured after 15-minute stirring in aqueous solutions of pH 1.2, 2, 3, 4 and 5 and in physiological saline solution, respectively, were excellent, being equal to or more than 95%.

EXAMPLE 46

| [Granule A composition] | |
|---|---|
| TMS-19-Q | 105.3 g |
| Glu.Na | 50.0 g |
| Light anhydrous silicic acid | 25.0 g |
| HPMC | 7.0 g |
| [Granule B composition] | |
| Glu.Na | 100.0 g |
| Tartaric acid | 35.0 g |

-continued

| | |
|---|---|
| Light anhydrous silicic acid | 10.0 g |
| HPMC | 5.0 g |
| [Excipient etc.] | |
| L-HPC | 30.0 g |
| Avicel pH 301 | 6.7 g |
| Magnesium stearate | 6.0 g |
| Total | 380.0 g |

By applying the same procedures as those of Example 45, capsules, each (380 mg) of which contains 100 mg potency of TMS-19-Q, 150 mg of Glu.Na and 35 mg of tartaric acid were obtained.

The elution rate measurements by the stirrer method, in which 2 capsules were used gave excellent results, showing that at each level of pH the elution rate after 15-minute stirring was equal to or more than 95%.

We claim:

1. A stable oral preparation of a 16-membered ring macrolide antibiotic with increased resistance to dissolution by gastric juices and adequate bioavailability which comprises a 9-hydroxy or 9-acyloxy 16-membered ring macrolide and an effective amount of a stabilizer therefor, said stabilizer exhibiting a pH of 3–65 in aqueous solution and being present in an amount of at least 10 mg per 100 mg potency of said antiobiotic, said antibiotic having the formula

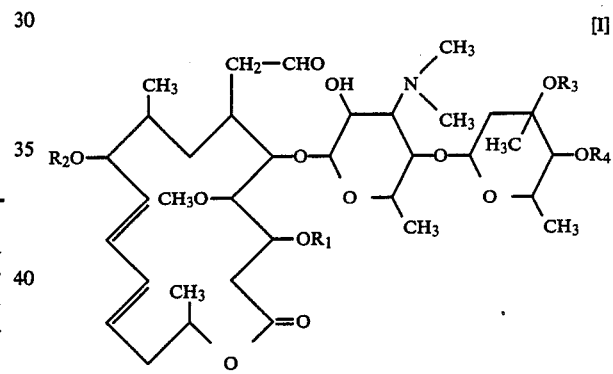

wherein each of $R_1$, $R_2$ and $R_3$ independent of the other is hydrogen or lower alkanoyl, and $R_4$ is lower alkanoyl, and said stabilizer being selected from the group consisting of neutral amino acids monosodium or monopotassum salt of acidic amino acids, basic amino acids, sodium or potassium salts of mono-basic and polybasic organic carboxylic acids, calcium phosphate, aluminum glycinate and mixtures thereof.

2. An oral preparation according to claim 1, wherein said 9-hydroxy or 9-acyloxy 16-membered ring macrolide anti-biotic is SF-837, josamycin, 3''-propionylleucomycin A₅, 9,3''-diacetyl SF-837 or 9-propionyljosamycin.

3. An oral preparation according to claim 1, wherein wherein said stabilizer is a neutral amino acid selected from the group consisting of glycine, alanine, aminobutyric acid, proline, leucine, isoleucine, threonine, and valine.

4. An oral preparation according to claim 1, wherein wherein said stabilizer is a mono-sodium or monopotassium salt of glutamic acid or aspartic acid.

5. An oral preparation according to claim 1, wherein said stabilizer is histidine.

6. An oral preparation according to claim 1, wherein said stabilizer is a sodium or potassium, salt of a monobasic organic carboxylic acid selected from the group consisting of lactic acid and pyruvic acid.

7. An oral preparation according to claim 1, wherein said stabilizer is a mono-, di-or tri-sodium or potassium, salt of a polybasic organic carboxylic acid selected from the group consisting of malonic acid, succinic acid, glutaric acid adipic acid, pimelic acid, maleic acid, humaric acid, meso-oxalic acid, malic acid, oxalacetic acid, tartaric acid and citric acid.

8. An oral preparation according to claim 1, further comprising a dissolution accelerator exhibiting a pH of 2.5–4 in aqueous solution in an amount of at least 5 mg per 100 mg potency of the 16-membered ring macrolide antibiotic, wherein said dissolution accelerator is a monobasic organic carboxylic acid, polybasic organic carboxylic acid or acidic monobasic salt thereof, monobasic salt of an acidic polybasic inorganic acid or a mixture thereof.

9. An oral preparation according to claim 8, where in said dissolution accelerator is a monobasic organic carboxylic acid selected from the group consisting of acetic acid, propionic acid, acrylic acid, crotonic acid, vinylacetic acid, lactic acid, pyruvic acid, glyceric acid and acetoacetic acid.

10. An oral preparation according to claim 8, wherein said dissolution accelerator is a polybasic organic carboxylic acid selected from the group consisting of oxalic acid, malonic acid, succinic acid, glutaric acid, adipic acid, pimelic acid, maleic acid, fumaric acid, tartaric acid, malic acid, meso-oxalic acid, oxalacetic acid and citric acid, or a monosodium or monopotassium salt thereof.

11. An oral preparation according to claim 8, where in said dissolution accelerator is sodium hydrogen phosphate or potassium dihydrogen phosphate.

12. A method for providing 16 membered ring macrolide antibiotic with increased resistance to dissolution by gastric juices and adequate bioavailability said antibiotic having the formula

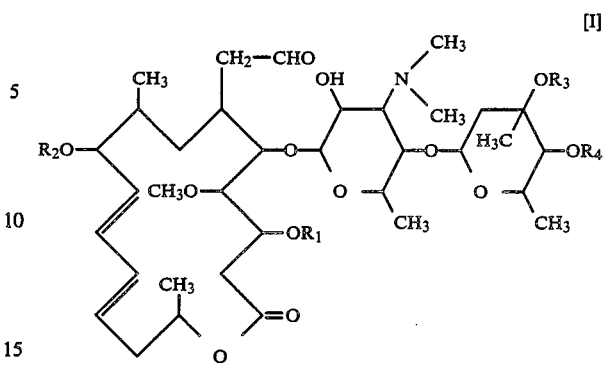

wherein each of $R_1$, $R_2$ and $R_3$ independent of the others is hydrogen or lower alkanoyl, and $R_4$ is lower alkanoyl, comprising adding to said antibiotic an effective amount of a stabilizer selected from the group consisting of neutral amino acids and basis salts thereof, basis salts of acidic amino acids, basic amino acids, basic salts of monobasic and polybasic organic carboxylic acids, basic salts of uric acids, inorganic salt antacids and mixtures thereof.

13. A method as in claim 12 wherein antibiotic is SF-837, josamycin, 3''-propionylleucomycin $A_5$, 9,3''-diacetyl SF-837 or 9-propionyljosamycin.

14. A method as in claim 12 wherein said stabilizer is a neutral amino acid selected from the group consisting of glycine, alanine, aminobutyric acid, leucine, isoleucine, threonine, and valine.

15. A method as in claim 12 wherein said stabilizer is a monosodium or monopotassium salt of glutamic acid or aspartic acid.

16. A method as in claim 12 wherein said stabilizer is histidine.

17. A method as in claim 12 wherein said stabilizer is a sodium or potassium, salt of a monobasic organic carboxylic acid selected from the group consisting of lactic acid and pyruvic acid.

18. A method as in claim 12 wherein said stabilizer is a mono-, di-or tri-sodium or potassium salt of a polybasic organic carboxylic acid selected from the group consisting of malonic acid, succinic acid, glutaric acid and citric acid.

* * * * *